US 8,084,221 B2

(12) United States Patent
Sprague et al.

(10) Patent No.: US 8,084,221 B2
(45) Date of Patent: Dec. 27, 2011

(54) METHOD OF SCREENING FOR A DRUG CANDIDATE THAT INCREASES ATP RELEASE FROM RBCS STIMULATED VIA THE GS OR GI PATHWAY

(75) Inventors: Randy S Sprague, St. Louis, MO (US); Madelyn Stumpf, Saint Louis, MO (US)

(73) Assignee: Saint Louis University, Saint Louis, MO (US)

( * ) Notice: Subject to any disclaimer, the term of this patent is extended or adjusted under 35 U.S.C. 154(b) by 470 days.

(21) Appl. No.: 11/695,102

(22) Filed: Apr. 2, 2007

(65) Prior Publication Data

US 2007/0249668 A1     Oct. 25, 2007

Related U.S. Application Data

(60) Provisional application No. 60/788,584, filed on Apr. 1, 2006.

(51) Int. Cl.
*G01N 33/53*     (2006.01)
(52) U.S. Cl. ........................................................ 435/7.2
(58) Field of Classification Search ........................ None
See application file for complete search history.

(56) References Cited

OTHER PUBLICATIONS

Sun et al., "New Mechanism of Action of Cilostazol: Interplay Between Adenosine and Cilostazol in Inhibiting Platelet Activation", J. Cardiovascular Pharmacology 40 (4) : 577-585 (2002).*
Bergfeld et al, Release of ATP from human erythrocytes in response to a brief period of hypoxia and hypercapnia, Cardiovasc Res, 1992, 26(1):40-47.
Ellsworth et al, The erythrocyte as a regulator of vascular tone. Am J Physiol, 1995. 269(6 Pt 2): p. H2155-61.
Ellsworth, The red blood cell as an oxygen sensor: what is the evidence? Acta Physiol Scand, 2000. 168(4): p. 551-9.
Ellsworth, Red blood cell-derived ATP as a regulator of skeletal muscle perfusion. Med Sci Sports Exerc, 2004. 36(1): p. 35-41.
Jagger et al, Role of erythrocyte in regulating local O2 delivery mediated by hemoglobin oxygenation. Am J Physiol Heart Circ Physiol, 2001. 280(6): p. H2833-9.
Sprague et al, ATP: the red blood cell link to NO and local control of the pulmonary circulation. Am J Physiol, 1996. 271(6 Pt 2): p. H2717-22.
Sprague et al, Extracellular ATP signaling in the rabbit lung: erythrocytes as determinants of vascular resistance. Am J Physiol Heart Circ Physiol, 2003. 285(2): p. H693-700.
Olearczyk et al, Receptor-mediated activation of the heterotrimeric G-protein Gs results in ATP release from erythrocytes. Med Sci Monit, 2001. 7(4): p. 669-74.
Olearczyk et al, Heterotrimeric G protein Gi is involved in a signal transduction pathway for ATP release from erythrocytes. Am J Physiol Heart Circ Physiol, 2004. 286(3): p. H940-5.
Sprague et al, Participation of cAMP in a signal-transduction pathway relating erythrocyte deformation to ATP release. Am J Physiol Cell Physiol, 2001. 281(4): p. C1158-64.
Sprague et al, Rabbit erythrocytes possess adenylyl cyclase type II that is activated by the heterotrimeric G proteins Gs and Gi. Pharmacol Rep, 2005. 57 Suppl: p. 222-8.
Sprague et al, Reduced expression of G(i) in erythrocytes of humans with type 2 diabetes is associated with impairment of both cAMP generation and ATP release. Diabetes, 2006. 55(12): p. 3588-93.
Sandeman et al, Microvascular vasodilatation in feet of newly diagnosed non-insulin dependent diabetic patients. Bmj, 1991. 302(6785): p. 1122-3.
Weir et al, Insulin Secretion in Type 2 Diabetes Mellitus, in Diabetes Mellitus: A Fundamental and Clinical Text, D. Leroith, S. I. Taylor, and J. M. Olefsky, Editors. 2004, Lippincott Williams and Wilkins: Philadelphia, Pa. p. 887-898.
Jaap et al, Reduced microvascular hyperaemia in subjects at risk of developing type 2 (non-insulin-dependent) diabetes mellitus. Diabetologia, 1994. 37(2): p. 214-6.
Degerman et al, Structure, localization, and regulation of cGMP-inhibited phosphodiesterase (PDE3). J Biol Chem, 1997. 272(11): p. 6823-6.
Degerman et al, Role for Phosphoidesterase 3B in Regulation of Lipolysis and Insulin Secretion, in Diabetes Mellitus: A Fundamental and Clinical Text, D. Leroith, S. I. Taylor, and J. M. Olefsky, Editors. 2004, Lippincott Williams & Wilkins: Philadephia, Pa.
Rahn et al, Essential role of phosphatidylinositol 3-kinase in insulin-induced activation and phosphorylation of the cGMP-inhibited cAMP phosphodiesterase in rat adipocytes. Studies using the selective inhibitor wortmannin. FEBS Lett, 1994. 350(2-3): p. 314-8.
Rondinone et al, Phosphorylation of PDE3B by phosphatidylinositol 3-kinase associated with the insulin receptor. J Biol Chem, 2000. 275(14): p. 10093-8.
Shakur et al, Regulation and function of the cyclic nucleotide phosphodiesterase (PDE3) gene family. Prog Nucleic Acid Res Mol Biol, 2001. 66: p. 241-77.
Gambhir et al, Characteristics of human erythrocyte insulin receptors. Diabetes, 1978. 27(7): p. 701-8.
Gherzi et al, Insulin receptor regulation in human mature red cells in vitro. Horm Res, 1985. 22(4): p. 270-5.
Ward et al, Structure of the human erythrocyte insulin receptor. Diabetes, 1986. 35(1): p. 101-5.

(Continued)

*Primary Examiner* — Sandra Saucier
(74) *Attorney, Agent, or Firm* — Armstrong Teasdale LLP

(57) ABSTRACT

The invention is based upon the discovery that red blood cells contain phosphodiesterase 3B (PDE3B), and that inhibition of that phosphodiesterase allows for an enhanced accumulation of cAMP and subsequent release of ATP. It was further discovered that RBCs treated with insulin accumulate significantly less cAMP and release significantly less ATP than normal RBCs. Likewise, RBCs of patients suffering from type 2 diabetes (hyperinsulinemia) accumulate significantly less cAMP and release significantly less ATP than normal RBCs. It was further discovered that prostaglandin analogues synergistically work with phosphodiesterase 3B inhibitors to improve or increase cAMP accumulation and ATP release by RBCs. Thus the invention is directed to compositions and methods for improving ATP release by RBCs, via administering PDE3B inhibitor or a combination of PDE3B inhibitor and prostaglandin analogue.

6 Claims, 20 Drawing Sheets

OTHER PUBLICATIONS

Sauvage et al, Insulin stimulates NHE1 activity by sequential activation of phosphatidylinositol 3-kinase and protein kinase C zeta in human erythrocytes. Eur J Biochem, 2000. 267(4): p. 955-62.

McCullough et al, Arteriolar responses to extracellular ATP in striated muscle. Am J Physiol, 1997. 272(4 Pt 2): p. H1886-91.

Bayewitch et al, Differential modulation of adenylyl cyclases I and II by various G beta subunits. J Biol Chem, 1998. 273(4): p. 2273-6.

Federman et al, Hormonal stimulation of adenylyl cyclase through Gi-protein beta gamma subunits. Nature, 1992. 356(6365): p. 159-61.

Dreiling, Localization of 2',3'-cyclic nucleotide 3'-phosphodiesterase in human erythrocyte membranes. Biochim Biophys Acta, 1981. 649(3): p. 587-94.

Hemington et al, Cyclic nucleotide phosphodiesterase activity in the plasma and erythrocytes of normal and diabetic rats Biochim Biophys Acta, 1973. 304(2): p. 552-9.

Petrov et al, Human erythrocytes contain Ca2+, calmodulin-dependent cyclic nucleotide phosphodiesterase which is involved in the hydrolysis of cGMP. Methods Find Exp Clin Pharmacol, 1998. 20(5): p. 387-93.

Ding et al, Functional role of phosphodiesterase 3 in cardiomyocyte apoptosis: implication in heart failure. Circulation, 2005. 111(19): p. 2469-76.

Hamdahl et al, Important role of phosphodiesterase 3B for the stimulatory action of cAMP on pancreatic beta-cell exocytosis and release of insulin. J Biol Chem, 2002. 277 (40): p. 37446-55.

Hermsdorf et al, Combined effects of insulin and dexamethasone on cyclic AMP phosphodiesterase 3 and glycogen metabolism in cultured rat hepatocytes. Cell Signal, 1998. 10(9): p. 629-35.

Wijkander et al, Insulin-induced phosphorylation and activation of phosphodiesterase 3B in rat adipocytes: possible role for protein kinase B but not mitogen-activated protein kinase or p70 S6 kinase. Endocrinology, 1998. 139(1): p. 219-27.

Resjo et al, Phosphorylation and activation of phosphodiesterase type 3B (PDE3B) in adipocytes in response to serine/threonine phosphatase inhibitors: deactivation of PDE3B in vitro by protein phosphatase type 2A. Biochem J, 1999. 341 (Pt 3): p. 839-45.

Freidenberg et al, Insulin binding to erythrocytes incubated in vitro at physiological temperature. J Clin Endocrinol Metab, 1983. 57(1): p. 107-14.

Suzuki et al, Characterization of the insulin receptor kinase from human erythrocytes. Endocrinology, 1987. 121(3): p. 972-9.

Zancan et al, Calcium influx: a possible role for insulin modulation of intracellular distribution and activity of 6-phosphofructo-1-kinase in human erythrocytes. Mol Genet Metab, 2005. 86(3): p. 392-400.

Kim et al, Signalling through IGF-I and insulin receptors: where is the specificity? Growth Horm IGF Res, 2002. 12(2): p. 84-90.

Jansen et al, Insulin-like growth factor I receptors on blood cells: their relationship to circulating total and "free" IGF-I, IGFBP-1, IGFBP-3 and insulin levels in healthy subjects. Growth Horm IGF Res, 1998. 8(1): p. 47-54.

Zhao et al, Attenuation of insulin secretion by insulin-like growth factor 1 is mediated through activation of phosphodiesterase 3B. Proc Natl Acad Sci USA, 1997. 94 (7): p. 3223-8.

Hizuka et al, Characterization of insulin-like growth factor I receptor on human erythrocytes. J Clin Endocrinol Metab, 1985. 61(6): p. 1066-70.

Liu et al, Cilostazol (pletal): a dual inhibitor of cyclic nucleotide phosphodiesterase type 3 and adenosine uptake. Cardiovasc Drug Rev, 2001. 19(4): p. 369-86.

De Meyts, The structural basis of insulin and insulin-like growth factor-I receptor binding and negative co-operativity, and its relevance to mitogenic versus metabolic signalling. Diabetologia, 1994. 37 Suppl 2: p. S135-48.

Dutta-Roy et al, Prostaglandin-E1-binding sites in rabbit erythrocyte membranes. Eur J Biochem, 1993. 213(3): p. 1167-73.

Olearczyk et al, Nitric oxide inhibits ATP release from erythrocytes. J Pharmacol Exp Ther, 2004. 309(3): p. 1079-84.

Zancan et al, Regulation of human erythrocyte metabolism by insulin: cellular distribution of 6-phosphofructo-1-kinase and its implication for red blood cell function. Mol Genet Metab, 2005. 86(3): p. 401-11.

Sager, Receptor binding sites for beta-adrenergic ligands on human erythrocytes. Biochem Pharmacol, 1982. 31(1): p. 99-104.

Hei et al, Lack of correlation between activation of cyclic AMP-dependent protein kinase and inhibition of contraction of rat vas deferens by cyclic AMP analogs. Mol Pharmacol, 1991. 39(2): p. 233-8.

Ho et al, Structural requirements for the edema-inducing and hemolytic activities of mastoparan B isolated from the hornet (*Vespa basalis*) venom. Toxicon, 1996. 34(9): p. 1027-35.

Kitamura et al, Insulin-induced phosphorylation and activation of cyclic nucleotide phosphodiesterase 3B by the serine-threonine kinase Akt. Mol Cell Biol, 1999. 19(9): p. 6286-96.

Baltensperger et al, Catalysis of serine and tyrosine autophosphorylation by the human insulin receptor. Proc Natl Acad Sci USA, 1992. 89(17): p. 7885-9.

Shakur et al, Comparison of the effects of cilostazol and milrinone on cAMP-PDE activity, intracellular cAMP and calcium in the heart. Cardiovasc Drugs Ther, 2002. 16 (5): p. 417-27.

Gonzalez et al, Insulin signaling diverges into Akt-dependent and -independent signals to regulate the recruitment/docking and the fusion of GLUT4 vesicles to the plasma membrane. Mol Biol Cell, 2006. 17(10): p. 4484-93.

Degerman et al, Evidence that insulin and isoprenaline activate the cGMP-inhibited low-Km cAMP phosphodiesterase in rat fat cells by phosphorylation. Proc Natl Acad Sci USA, 1990. 87(2): p. 533-7.

Moroi et al, Integrin-mediated platelet adhesion. Front Biosci, 1998. 3: p. d719-28.

De Meyts et al, Structural biology of insulin and IGF1 receptors: implications for drug design. Nat Rev Drug Discov, 2002. 1(10): p. 769-83.

Avruch, Small GTPases and Serine/Threonine Protein Kinase Cascades in Insulin Signal Transduction, in Diabetes Mellitus: A Fundamental and Clinical Text, D. Leroith, S.T. Taylor and J.M. Olefsky, Editors. 2004, Lippincott Williams & Wilkins: Philadelphia, Pa. p. 269-299.

Higashijima et al, Regulation of Gi and Go by mastoparan, related amphiphilic peptides, and hydrophobic amines, Mechanism and structural determinants of activity. J Biol Chem, 1990. 265(24): p. 14176-86.

Van Horn et al, Direct activation of the phosphatidylipositol 3'-kinase by the insulin receptor. J Biol Chem, 1994, 269 (1): p. 29-32.

Record et al, Phosphatidylinositol 3-kinase activation is required for insulin-stimulated sodium transport in A6 cells. Am J Physiol, 1998. 274(4 Pt 1): p. E611-7.

Liang et al, Erythrocytes of humans with cystic fibrosis fail to stimulate nitric oxide synthesis in isolated rabbit lungs. Am. J. Physiol. Heart Circ. Physiol. 288: pp. H1580-1585, 2005.

Sprague et al, Effect of L-NAME on pressure-flow relationships in solated rabbit lungs: role of red blood cells. Am J Physiol, Heart Circ Physiol. 269: pp. H1941-1948, 1995.

Sprague et al, Inhibition of nitric oxide synthesis results in a selective increase in arterial resistance in rabbit lungs. Pol J Pharmacol 46: pp. 579-585, 1994.

Sprague et al, Increases in perfusate flow rate stimulate ATP release from red blood cells in isolated rabbit lungs. Exp. Clin. Cardiol. 3(2): pp. 73-77, 1998.

Dietrich et al, Red blood cell regulation of microvascular tone through adenosine triphosphate. Am. J. Physiol. Heart Circ. Physiol. 278: pp. H1294-H1298, 2000.

Sprague et al, Impaired release of ATP from red blood cells of humans with primary pulmonary hypertension. Exp. Biol. Med. vol. 226(5): pp. 434-439, 2001.

Lobato et al, Treatment with phosphodiesterase inhibitors type III and V: milrinone and sildenafil is an effective combination during thromboxane-induced acute pulmonary hypertension. Br J Anaesth 95: pp. 317-322, 2006.

Sprague et al, "Red Blood Cell-Derived ATP is a Determinant of Nitric Oxide Synthesis in the Pulmonary Circulation," Chapter 9 in: Interactions of Blood and the Pulmonary Circulation, Weir, Reeve and Reeves (ed), Futura Publishing Co., Inc., Armonk, N.Y. 2002.

Sprague et al, The role of G protein B subunits in the release of ATP from human erythrocytes. J. Physiol Pharmacol 53(4): pp. 667-674, 2002.

Olearczyk et al, NO inhibits signal transduction pathway for ATP rlease from erythrocytes via its action on heterotrimeric G protein Gi. Am. J. Physiol. Heart Circ. Physiol. 287: pp. H748-H754, 2004.

Sprague et al, Deformation-induced ATP release from red blood cells requires CFTR activity. Am J Physiol, 1998. 275(5 Pt 2): p. H1726-32.

Jaap et al, Relationship of insulin resistence to microvascular dysfunction in subjects with fasting hyperglycemia. Diabetologia, 1997. 40(2): p. 238-43.

Glueck, Insulin Resistance and Hyperinsulinemia. 2005. Cincinatti, Ohio.

Harano et al, Development of cookie test for the simultaneous determination of glucose intolerance hyperinsulinemia, insulin resistance and postprandial dyslipidemia. Endocr J, 2006. 53(2): p. 173-80.

Lugnier, Cyclic nucleotide phosphodiesterase (PDE) superfamily: a new target for the development of specific therapeutic agents. Pharmacol Ther, 2006. 109(3): p. 366-98.

Bauman et al, Ontogeny of catecholamine and adenosine receptor-mediated cAMP signaling of embryonic red blood cells, role of cGMP-inhibited phosphodiesterase 3 and hemoglobin. Blood, 1999. 94(12): p. 4314-20.

Patterson et al, Apparent multiple forms of cyclic aMP phosphodiesterase from rat erythrocytes. Mol Cell Endocrinol, 1976. 5(1-2): p. 51-66.

Haslam et al, Cyclic nucleotides and phosphodiesterases in platelets. Thromb Haemost, 1999. 82(2): p. 412-2.

Rascon et al, Identification of the phosphorylation site in vitro for cAMP-dependent protein kinase on the rat adipocyte cGMP-inhibited cAMP phosphodiesterase. J Biol Chem, 1994. 269(16): p. 11962-11966.

Robinson et al, Erythrocytes: a new cell type for the evaluation of insulin receptor defects in diabetic humans. Science, 1979. 205(4402): p. 200-2.

\* cited by examiner

METHOD OF SCREENING FOR A DRUG CANDIDATE THAT INCREASES ATP RELEASE FROM RBCS STIMULATED VIA THE GS OR GI PATHWAY

PARENT CASE TEXT

This application claims priority to U.S. Provisional Patent Application No. 60/788,584, which was filed on Apr. 1, 2006.

BACKGROUND OF THE INVENTION

1. Field of the Invention

The invention is directed generally to compositions and methods for controlling vascular tension in extremities to improve blood flow at extremities and control pulmonary blood pressure. More specifically, the invention is directed to the control of ATP release by red blood cells, via manipulating phosphodiesterase 3 in red blood cells using inhibitors of phosphodiesterase 3.

2. Description of the Related Art

It is known in the art that shear stress in arterioles stimulates the production of endothelium relaxation factors that act on the smooth muscle cells of arterioles, causing the vessels to relax and permit increased blood flow. An example of an endothelium relaxation factor is nitric oxide. Work performed by the inventors and collaborators have suggested that red blood cells, while under conditions of low oxygen tension or cell deformation (e.g., as RBCs squeeze through smaller vessels), release ATP into the blood vessel lumen. The ATP released from red blood cells, in turn leads to NO synthesis and release of endothelium derived relaxation factors by the endothelial cells, which enables vasorelaxation.

It has also been shown by the inventors that patients with certain diseases produce red blood cells which release none to subnormal levels of ATP in response to low oxygen tension or under mechanical deformation. Those diseases include (but are certainly not envisioned to be limited to) diabetes, cystic fibrosis, hyperinsulinemia, type 2 diabetes, and primary pulmonary hypertension. The inventors envision that RBCs are an important system for the regulation of blood flow into areas and conditions of low oxygen tension, and subject to mechanical deformities such as in capillary beds and at extremities. The invention discloses (a) the mechanism by which RBCs can release ATP, (b) compositions to enhance the production of ATP by RBCs, and (c) methods of treating diseases such as pulmonary hypertension and diabetic blood flow problems.

The erythrocyte, by virtue of the hemoglobin that it contains, has long been recognized as a vehicle for oxygen (O2) transport. In addition to this well established role for the erythrocyte in the circulation, it has been shown that this cell can also participate in the regulation of vascular resistance via the release of ATP [2-8]. The erythrocyte releases ATP when exposed to reduced O2 tension or mechanical deformation, as well as in response endogenous mediators [1, 2, 4, 7, 9, 11, 13]. This erythrocyte-derived ATP has been shown to be a stimulus for NO synthesis [3, 7, 8]. The ability of the erythrocyte to release ATP in response to physiological stimuli enables this cell to control its own distribution within the microcirculation and, thereby, to regulate O2 delivery [2-4, 6]. Indeed, it has been proposed that the erythrocyte, via its ability to release ATP in response to reduced O2 tension, produces local vasodilation in areas of skeletal muscle with increased O2 demand resulting in the matching of O2 delivery with metabolic need [2, 5, 6, 30].

Recently, the inventors have defined a signal transduction pathway that relates physiological and pharmacological stimuli to ATP release from erythrocytes [12]. This pathway includes the heterotrimeric G proteins Gi and Gs, adenylyl cyclase (AC), cyclic adenosine monophosphate (cAMP), protein kinase A (PKA), and the cystic fibrosis transmembrane conductance regulator (CFTR) (FIG. 10) [9-13]. It is important to note that, in this pathway, activation of either Gs or Gi results in the stimulation of AC activity and cAMP synthesis [9, 10]. The finding that activation of Gi is capable of stimulating some AC subtypes is not unique to the erythrocyte [31, 32]. It has been reported that, in multiple cell types, AC type II is activated by the βγ subunit of Gi [10, 12, 14, 31, 32]. We have shown that both Gi and AC type II are components of human erythrocyte membranes [10, 14].

As depicted in FIG. 10, increases in cAMP are required for ATP release from erythrocytes [11]. The level of cAMP in a cell is the product of its synthesis by AC and its degradation by phosphodiesterases (PDEs) [33]. In addition to AC II, it is known in the art that human (any and all) erythrocytes possess PDE activity, however, neither the PDE subtypes present nor their regulation have yet to be fully characterized [12, 14, 34-38].

REFERENCES

The following references are cited throughout this disclosure and are incorporated by reference. They serve to illustrate the background art. The inventors reserve the right to challenge the veracity of any statements made therein.

1. Bergfeld, G. R. and T. Forrester, Release of ATP from human erythrocytes in response to a brief period of hypoxia and hypercapnia. Cardiovasc Res, 1992. 26(1): p. 40-7.
2. Ellsworth, M. L., et al., The erythrocyte as a regulator of vascular tone. Am J Physiol, 1995. 269(6 Pt 2): p. H2155-61.
3. Ellsworth, M. L., The red blood cell as an oxygen sensor: what is the evidence? Acta Physiol Scand, 2000. 168(4): p. 551-9.
4. Dietrich, H. H., et al., Red blood cell regulation of microvascular tone through adenosine triphosphate. Am J Physiol Heart Circ Physiol, 2000. 278(4): p. H1294-8.
5. Ellsworth, M. L., Red blood cell-derived ATP as a regulator of skeletal muscle perfusion. Med Sci Sports Exerc, 2004. 36(1): p. 35-41.
6. Jagger, J. E., et al., Role of erythrocyte in regulating local O2 delivery mediated by hemoglobin oxygenation. Am J Physiol Heart Circ Physiol, 2001. 280(6): p. H2833-9.
7. Sprague, R. S., et al., ATP: the red blood cell link to NO and local control of the pulmonary circulation. Am J Physiol, 1996. 271(6 Pt 2): p. H2717-22.
8. Sprague, R. S., et al., Extracellular ATP signaling in the rabbit lung: erythrocytes as determinants of vascular resistance. Am J Physiol Heart Circ Physiol, 2003. 285(2): p. H693-700.
9. Olearczyk, J. J., et al., Receptor-mediated activation of the heterotrimeric G protein Gs results in ATP release from erythrocytes. Med Sci Monit, 2001. 7(4): p. 669-74.
10. Olearczyk, J. J., et al., Heterotrimeric G protein Gi is involved in a signal transduction pathway for ATP release from erythrocytes. Am J Physiol Heart Circ Physiol, 2004. 286(3): p. H940-5.

11. Sprague, R. S., et al., Participation of cAMP in a signal-transduction pathway relating erythrocyte deformation to ATP release. Am J Physiol Cell Physiol, 2001. 281(4): p. C1158-64.
12. Sprague, R., et al., Rabbit erythrocytes possess adenylyl cyclase type II that is activated by the heterotrimeric G proteins Gs and Gi. Pharmacol Rep, 2005. 57 Suppl: p. 222-8.
13. Sprague, R. S., et al., Deformation-induced ATP release from red blood cells requires CFTR activity. Am J Physiol, 1998. 275(5 Pt 2): p. H1726-32.
14. Sprague, R. S., et al., Reduced expression of G(i) in erythrocytes of humans with type 2 diabetes is associated with impairment of both cAMP generation and ATP release. Diabetes, 2006. 55(12): p. 3588-93.
15. Sandeman, D. D., et al., Microvascular vasodilatation in feet of newly diagnosed non-insulin dependent diabetic patients. Bmj, 1991. 302(6785): p. 1122-3.
16. Weir, G. and S. Bonner-Weir, Insulin Secretion in Type 2 Diabetes Mellitus, in Diabetes Mellitus: A Fundamental and Clinical Text, D. Leroith, S. I. Taylor, and J. M. Olefsky, Editors. 2004, Lippincott Williams and Wilkins: Philadelphia, Pa. p. 887-898.
17. Jaap, A. J., A. C. Shore, and J. E. Tooke, Relationship of insulin resistance to microvascular dysfunction in subjects with fasting hyperglycaemia. Diabetologia, 1997. 40 (2): p. 238-43.
18. Jaap, A. J., et al., Reduced microvascular hyperaemia in subjects at risk of developing type 2 (non-insulin-dependent) diabetes mellitus. Diabetologia, 1994. 37(2): p. 214-6.
19. Degerman, E., P. Belfrage, and V. C. Manganiello, Structure, localization, and regulation of cGMP-inhibited phosphodiesterase (PDE3). J Biol Chem, 1997. 272(11): p. 6823-6.
20. Degerman, E., et al., Role for Phosphoidesterase 3B in Regulation of Lipolysis and Insulin Secretion, in Diabetes Mellitus: A Fundamental and Clinical Text, D. Leroith, S. I. Taylor, and J. M. Olefsky, Editors. 2004, Lippincott Williams & Wilkins: Philadelphia, Pa.
21. Rahn, T., et al., Essential role of phosphatidylinositol 3-kinase in insulin-induced activation and phosphorylation of the cGMP-inhibited cAMP phosphodiesterase in rat adipocytes. Studies using the selective inhibitor wortmannin. FEBS Lett, 1994. 350(2-3): p. 314-8.
22. Rondinone, C. M., et al., Phosphorylation of PDE3B by phosphatidylinositol 3-kinase associated with the insulin receptor. J Biol Chem, 2000. 275(14): p. 10093-8.
23. Shakur, Y., et al., Regulation and function of the cyclic nucleotide phosphodiesterase (PDE3) gene family. Prog Nucleic Acid Res Mol Biol, 2001. 66: p. 241-77.
24. Gambhir, K. K., J. A. Archer, and C. J. Bradley, Characteristics of human erythrocyte insulin receptors. Diabetes, 1978. 27(7): p. 701-8.
25. Gherzi, R., et al., Insulin receptor regulation in human mature red cells in vitro. Horm Res, 1985. 22(4): p. 270-5.
26. Ward, G. M. and L. C. Harrison, Structure of the human erythrocyte insulin receptor. Diabetes, 1986. 35(1): p. 101-5.
27. Sauvage, M., et al., Insulin stimulates NHE1 activity by sequential activation of phosphatidylinositol 3-kinase and protein kinase C zeta in human erythrocytes. Eur J Biochem, 2000. 267(4): p. 955-62.
28. Glueck, C., Insulin Resistance and Hyperinsulinemia. 2005: Cincinnati, Ohio.
29. Harano, Y., et al., Development of cookie test for the simultaneous determination of glucose intolerance, hyperinsulinemia, insulin resistance and postprandial dyslipidemia. Endocr J, 2006. 53(2): p. 173-80.
30. McCullough, W. T., D. M. Collins, and M. L. Ellsworth, Arteriolar responses to extracellular ATP in striated muscle. Am J Physiol, 1997. 272(4 Pt 2): p. H1886-91.
31. Bayewitch, M. L., et al., Differential modulation of adenylyl cyclases I and II by various G beta subunits. J Biol Chem, 1998. 273(4): p. 2273-6.
32. Federman, A. D., et al., Hormonal stimulation of adenylyl cyclase through Gi-protein beta gamma subunits. Nature, 1992. 356(6365): p. 159-61.
33. Lugnier, C., Cyclic nucleotide phosphodiesterase (PDE) superfamily: a new target for the development of specific therapeutic agents. Pharmacol Ther, 2006. 109(3): p. 366-98.
34. Baumann, R., et al., Ontogeny of catecholamine and adenosine receptor-mediated cAMP signaling of embryonic red blood cells: role of cGMP-inhibited phosphodiesterase 3 and hemoglobin. Blood, 1999. 94(12): p. 4314-20.
35. Dreiling, C. E., Localization of 2',3'-cyclic nucleotide 3'-phosphodiesterase in human erythrocyte membranes. Biochim Biophys Acta, 1981. 649(3): p. 587-94.
36. Hemington, J. G., M. Chenoweth, and A. Dunn, Cyclic nucleotide phosphodiesterase activity in the plasma and erythrocytes of normal and diabetic rats. Biochim Biophys Acta, 1973. 304(2): p. 552-9.
37. Patterson, W. D., J. G. Hardman, and E. W. Sutherland, Apparent multiple forms of cyclic AMP phosphodiesterase from rat erythrocytes. Mol Cell Endocrinol, 1976. 5(1-2): p. 51-66.
38. Petrov, V., R. Fagard, and P. Lijnen, Human erythrocytes contain Ca2+, calmodulin-dependent cyclic nucleotide phosphodiesterase which is involved in the hydrolysis of cGMP. Methods Find Exp Clin Pharmacol, 1998. 20(5): p. 387-93.
39. Ding, B., et al., Functional role of phosphodiesterase 3 in cardiomyocyte apoptosis: implication in heart failure. Circulation, 2005. 111(19): p. 2469-76.
40. Haslam, R. J., N. T. Dickinson, and E. K. Jang, Cyclic nucleotides and phosphodiesterases in platelets. Thromb Haemost, 1999. 82(2): p. 412-23.
41. Harndahl, L., et al., Important role of phosphodiesterase 3B for the stimulatory action of cAMP on pancreatic beta-cell exocytosis and release of insulin. J Biol Chem, 2002. 277(40): p. 37446-55.
42. Hermsdorf, T. and D. Dettmer, Combined effects of insulin and dexamethasone on cyclic AMP phosphodiesterase 3 and glycogen metabolism in cultured rat hepatocytes. Cell Signal, 1998. 10(9): p. 629-35.
43. Rascon, A., et al., Identification of the phosphorylation site in vitro for cAMP-dependent protein kinase on the rat adipocyte cGMP-inhibited cAMP phosphodiesterase. J Biol Chem, 1994. 269(16): p. 11962-6.
44. Wijkander, J., et al., Insulin-induced phosphorylation and activation of phosphodiesterase 3B in rat adipocytes: possible role for protein kinase B but not mitogen-activated protein kinase or p70 S6 kinase. Endocrinology, 1998. 139(1): p. 219-27.

45. Resjo, S., et al., Phosphorylation and activation of phosphodiesterase type 3B (PDE3B) in adipocytes in response to serine/threonine phosphatase inhibitors: deactivation of PDE3B in vitro by protein phosphatase type 2A. Biochem J, 1999. 341 (Pt 3): p. 839-45.

46. Robinson, T. J., et al., Erythrocytes: a new cell type for the evaluation of insulin receptor defects in diabetic humans. Science, 1979. 205(4402): p. 200-2.

47. Freidenberg, G. F., M. Kao, and J. M. Olefsky, Insulin binding to erythrocytes incubated in vitro at physiological temperature. J Clin Endocrinol Metab, 1983. 57(1): p. 107-14.

48. Suzuki, S., T. Toyota, and Y. Goto, Characterization of the insulin receptor kinase from human erythrocytes. Endocrinology, 1987. 121(3): p. 972-9.

49. Zancan, P. and M. Sola-Penna, Calcium influx: a possible role for insulin modulation of intracellular distribution and activity of 6-phosphofructo-1-kinase in human erythrocytes. Mol Genet Metab, 2005. 86(3): p. 392-400.

50. Kim, J. J. and D. Accili, Signalling through IGF-I and insulin receptors: where is the specificity? Growth Horm IGF Res, 2002. 12(2): p. 84-90.

51. Janssen, J. A., et al., Insulin-like growth factor I receptors on blood cells: their relationship to circulating total and "free" IGF-I, IGFBP-1, IGFBP-3 and insulin levels in healthy subjects. Growth Horm IGF Res, 1998. 8(1): p. 47-54.

52. Zhao, A. Z., et al., Attenuation of insulin secretion by insulin-like growth factor 1 is mediated through activation of phosphodiesterase 3B. Proc Natl Acad Sci USA, 1997. 94 (7): p. 3223-8.

53. Hizuka, N., et al., Characterization of insulin-like growth factor I receptor on human erythrocytes. J Clin Endocrinol Metab, 1985. 61(6): p. 1066-70.

54. Liu, Y., et al., Cilostazol (pletal): a dual inhibitor of cyclic nucleotide phosphodiesterase type 3 and adenosine uptake. Cardiovasc Drug Rev, 2001. 19(4): p. 369-86.

55. De Meyts, P. and J. Whittaker, Structural biology of insulin and IGF 1 receptors: implications for drug design. Nat Rev Drug Discov, 2002. 1(10): p. 769-83.

56. De Meyts, P., The structural basis of insulin and insulin-like growth factor-I receptor binding and negative co-operativity, and its relevance to mitogenic versus metabolic signalling. Diabetologia, 1994. 37 Suppl 2: p. S135-48.

57. Dutta-Roy, A. K., L. Hogue, and B. J. Paterson, Prostaglandin-El-binding sites in rabbit erythrocyte membranes. Eur J Biochem, 1993. 213(3): p. 1167-73.

58. Olearczyk, J. J., et al., Nitric oxide inhibits ATP release from erythrocytes. J Pharmacol Exp Ther, 2004. 309(3): p. 1079-84.

59. Avruch, J., Small GTPases and Serine/Threonine Protein Kinase Cascades in Insulin Signal Transduction, in Diabetes Mellitus: A Fundamental and Clinical Text, D. Leroith, S. I. Taylor, and J. M. Olefsky, Editors. 2004, Lippincott Williams & Wilkins: Philadelphia, Pa. p. 255-299.

60. Zancan, P. and M. Sola-Penna, Regulation of human erythrocyte metabolism by insulin: cellular distribution of 6-phosphofructo-1-kinase and its implication for red blood cell function. Mol Genet Metab, 2005. 86(3): p. 401-11.

61. Sager, G., Receptor binding sites for beta-adrenergic ligands on human erythrocytes. Biochem Pharmacol, 1982. 31(1): p. 99-104.

62. Hei, Y. J., et al., Lack of correlation between activation of cyclic AMP-dependent protein kinase and inhibition of contraction of rat vas deferens by cyclic AMP analogs. Mol Pharmacol, 1991. 39(2): p. 233-8.

63. Higashijima, T., J. Burnier, and E. M. Ross, Regulation of Gi and Go by mastoparan, related amphiphilic peptides, and hydrophobic amines. Mechanism and structural determinants of activity. J Biol Chem, 1990. 265(24): p. 14176-86.

64. Ho, C. L., et al., Structural requirements for the edema-inducing and hemolytic activities of mastoparan β isolated from the hornet (*Vespa basalis*) venom. Toxicon, 1996. 34(9): p. 1027-35.

65. Van Horn, D. J., M. G. Myers, Jr., and J. M. Backer, Direct activation of the phosphatidylinositol 3'-kinase by the insulin receptor. J Biol Chem, 1994. 269(1): p. 29-32.

66. Kitamura, T., et al., Insulin-induced phosphorylation and activation of cyclic nucleotide phosphodiesterase 3B by the serine-threonine kinase Akt. Mol Cell Biol, 1999. 19(9): p. 6286-96.

67. Baltensperger, K., et al., Catalysis of serine and tyrosine autophosphorylation by the human insulin receptor. Proc Natl Acad Sci USA, 1992. 89(17): p. 7885-9.

68. Record, R. D., et al., Phosphatidylinositol 3-kinase activation is required for insulin-stimulated sodium transport in A6 cells. Am J Physiol, 1998. 274(4 Pt 1): p. E611-7.

69. Shakur, Y., et al., Comparison of the effects of cilostazol and milrinone on cAMP-PDE activity, intracellular cAMP and calcium in the heart. Cardiovasc Drugs Ther, 2002. 16(5): p. 417-27.

70. Gonzalez, E. and T. E. McGraw, Insulin signaling diverges into Akt-dependent and -independent signals to regulate the recruitment/docking and the fusion of GLUT4 vesicles to the plasma membrane. Mol Biol Cell, 2006. 17(10): p. 4484-93.

71. Degerman, E., et al., Evidence that insulin and isoprenaline activate the cGMP-inhibited low-Km cAMP phosphodiesterase in rat fat cells by phosphorylation. Proc Natl Acad Sci USA, 1990. 87(2): p. 533-7.

72. Moroi, M. and S. M. Jung, Integrin-mediated platelet adhesion. Front Biosci, 1998. 3: p. d719-28.

Sprague et al., Am. J. Physiol. Heart Circ. Physiol. 271: pp. H2717-2722; 1996.

Laing et al., Am. J. Physiol. Heart Circ. Physiol. 288: pp. H1-6; 2005.

Sprague et al., Am. J. Physiol. Heart Circ. Physiol. 269: pp. H1941-1948; 1995.

Sprague et al., Pol. J. Pharmacol. 46: pp. 579-585; 1994.

Sprague et al., Am. J. Physiol. Heart Circ. Physiol. 275: pp. H1726-1732; 1998.

Sprague et al., Exp. Clin. Cardiol. 3(2): pp. 73-77; 1998.

Dietrich et al., Am. J. Physiol. Heart Circ. Physiol. 278: pp. H1294-1298; 2000.

Sprague et al., Exp. Biol. Med. Vol. 226(5): pp. 434-439; 2001.

Sprague et al., Am. J. Physiol. Cell Physiol. 281: pp. C1158-1164; 2001.

Lobato et al., Br. J. Anaesth 95: pp. 317-322; 2005.

Sprague et al., "Red Blood Cell-Derived ATP Is a Determinant of Nitric Oxide Synthesis in the Pulmonary Circulation," Ch. 9 in *Interactions of Blood and the Pulmonary Circulation*, Weir, Reeve and Reeves (ed), Futura Publishing Co., Inc., Armonk, N.Y.; 2002.

Sprague et al., J. Physiol. Pharmacol. 53(4): pp. 667-674; 2002.

Sprague et al., Am. J. Physiol. Heart Circ. Physiol. 285: pp. H693-700; 2003.

Olearczyk et al., Am. J. Physiol. Heart Circ. Physiol. 286: pp. H940-945; 2004.
Olearczyk et al., J. Pharmacol. Exp. Ther. 309: pp. 1079-1084; 2004.
Olearczyk et al., Am. J. Physiol. Heart Circ. Physiol. 287: pp. H748-754; 2004.

SUMMARY OF THE INVENTION

Having known that RBCs release ATP, and that pathway involves the G-proteins Gi and Gs, adenylyl cyclase, protein kinase A (PKA), and the cystic fibrosis transmembrane receptor (CFTR) (FIG. 1), the inventors made the surprising discovery that RBCs contain phosphodiesterase 3 (PDE3) and that PDE3 regulation can potentiate ATP release by RBCs (FIGS. 2 and 3). Thus, in one embodiment, the invention is directed to a method of enhancing the production of ATP by RBCs, by contacting RBCs with an inhibitor of PDE (e.g., IBMX), preferably a selective inhibitor of PDE3 (e.g., milrinone or cilostazol), more preferably the selective PDE3 inhibitor cilostazol. The RBCs can be ex vivo or in vivo, wherein in vivo includes within a human patient.

Given that it is known that patients suffering from pulmonary hypertension, cystic fibrosis, and having newly disclosed in this application that patients suffering from hyperinsulinemia, and/or type 2 diabetes have RBCs that fail to release suboptimal amounts of ATP, the inventors envision that PDE inhibitors can be indicated for patients suffering from those diseases, to reduce vascular resistance and the increase blood flow to extremities. Thus, in another embodiment, the invention is directed to treating patients suffering from vascular diseases associated with cystic fibrosis, pulmonary hypertension, hyperinsulinemia, diabetes, or the like by administering a therapeutic amount of PDE inhibitor to the patient. The USP and Physicians Desk Reference list PDE inhibitors that are presently approved for use in humans (pre-existing art). Those PDE inhibitors thus are preferred. However, improved PDE inhibitors, especially improved PDE3 inhibitors can be used in the practice of this invention. The preferred PDE3 inhibitor is cilostazol, which is currently indicated for peripheral vascular disease.

The inventors have also made the surprising discovery that RBCs from patients suffering from diabetes, namely type 2 diabetes, release suboptimal amounts of ATP in response to low oxygen tension and mechanical deformation (FIG. 4). The G-protein, Gi, which is critical in the formation and release of ATP by RBCs, was discovered to be reduced in diabetic RBCs (FIG. 5; black bars represent diabetic RBCs, white bars represent normal RBCs; western blot strip on left represent normal RBCs, those on the right are diabetic). It is known in the art that mastoparan 7 (MAS7) stimulates Gi, which in the case of RBCs, in turn stimulates adenylyl cyclase to produce cAMP and eventually increased ATP release. When diabetic (MAS7) stimulates Gi, which in the case of RBCs, in turn stimulates adenylyl cylcates to produce cAMP and eventually increased ATP release. When diabetic cells were treated with MAS7 and ATP release was measured, the inventors observed that ATP release decreased with an increase in hemoglobin glycation (hemoglobin A1c; FIG. 6), thus demonstrating the correlation between blood sugar and decreased ATP release. Knowing that (a) PDE3 is present in RBCs, (b) PDEs catalyze the hydrolysis of cAMP to form ATP, and thus reduce the pool of cAMP available for ATP production via PKA, and (c) inhibitors of PDE can increase the pool of cAMP available for ATP production, the inventors treated diabetic RBCs with the PDE3-specific inhibitor cilostazol (CILO, FIG. 7) and looked for a change in MAS7-induced ATP release. FIG. 7 summarizes those observations and clearly demonstrates the CILO-treated diabetic RBCs can release amounts of ATP not significantly different from the levels released by RBCs of healthy individuals upon stimulation via the Gi pathway. Thus, as described above, the inventors envision that PDE3 inhibitors (preferably cilostazol) can be administered to patients suffering from diabetes (particularly type 2 diabetes, but not excluding the potential for type 1 diabetes) to increase the release of ATP by RBCs in low oxygen tension conditions and under mechanical deformation, to increase blood flow to extremities.

It is known in the art that RBCs have insulin receptors, which has been exploited as a tool for studying insulin binding. However, the role of insulin in RBC activity has not been elucidated. The inventors have made the additional surprising discovery that insulin affects the Gi-mediated release of ATP by RBCs (summarized in FIG. 10). FIGS. 8 and 9 depict that RBCs incubated in the presence of insulin show decline in Gi-induced cAMP production and ATP release (respectively). Thus, in another embodiment, the invention is directed to treatment protocols for type 2 diabetes, comprising administering to a patient a therapeutically effective amount of a PDE3-specific inhibitor (preferably cilostazol), thereby improving blood flow to extremities.

Having made the discoveries that RBCs contain active PDE3, which impinges on the ATP release pathway of RBCs, which affects vasorelaxtion, the inventors envision that this can be used as a screening tool for drugs that affect blood flow to extremities, vasorelaxation and contraction, peripheral hypertension and pulmonary hypertension. Thus, in yet another embodiment, the invention is directed to a drug screening platform and methods for screening for those types of drugs, comprising contacting and RBC (normal, cystic fibrosis, diabetic, primary pulmonary hypertensive, human, rabbit, dog and the like) with a prospective drug candidate, stimulating the RBC via the Gi pathway (e.g., low oxygen, mechanical deformation, MAS7, and/or the like), and measuring ATP release.

The inventors have also made the surprising discovery that a combination of prostaglandins (or prostaglandin analogues) and PDE inhibitors provide a combinatorial or synergistic effect on ATP release by erythrocytes. Example prostaglandins and analogues include, but are not limited to, iloprost, UT-15C, prostaglandin I2 (PGI2). Examples of PDE inhibitors include pentoxifylline (PTOX), IBMX, milrinone, and cilostazol. Isoproteranol also affects how ATP is released by erythrocytes. FIGS. 17 and 18 show the effect of prostaglandin analogues on cAMP production in rabbit and human erythrocytes, respectively. FIGS. 12-16 depict the effects of prostaglandin analogues in combination with PDE inhibitors on ATP production by RBCs. Thus, in another embodiment, the invention is directed to compositions, which are useful for increasing ATP production or release by erythrocytes, comprising prostaglandins or analogues thereof and PDE inhibitors. In an alternative embodiment, the invention is also directed to methods of treating diseases associated with increased vascular resistance, including but not limited to cystic fibrosis, pulmonary hypertension, hyperinsulinemia, and type 2 diabetes. In both of these embodiments, a preferred prostaglandin analogue is iloprost and a preferred PDE inhibitor is a PDE3 inhibitor, cilostazol.

BRIEF DESCRIPTION OF THE DRAWINGS

The drawings and concomitant descriptions are incorporated into this disclosure.

DETAILED DESCRIPTION OF THE INVENTION

Figure 10:
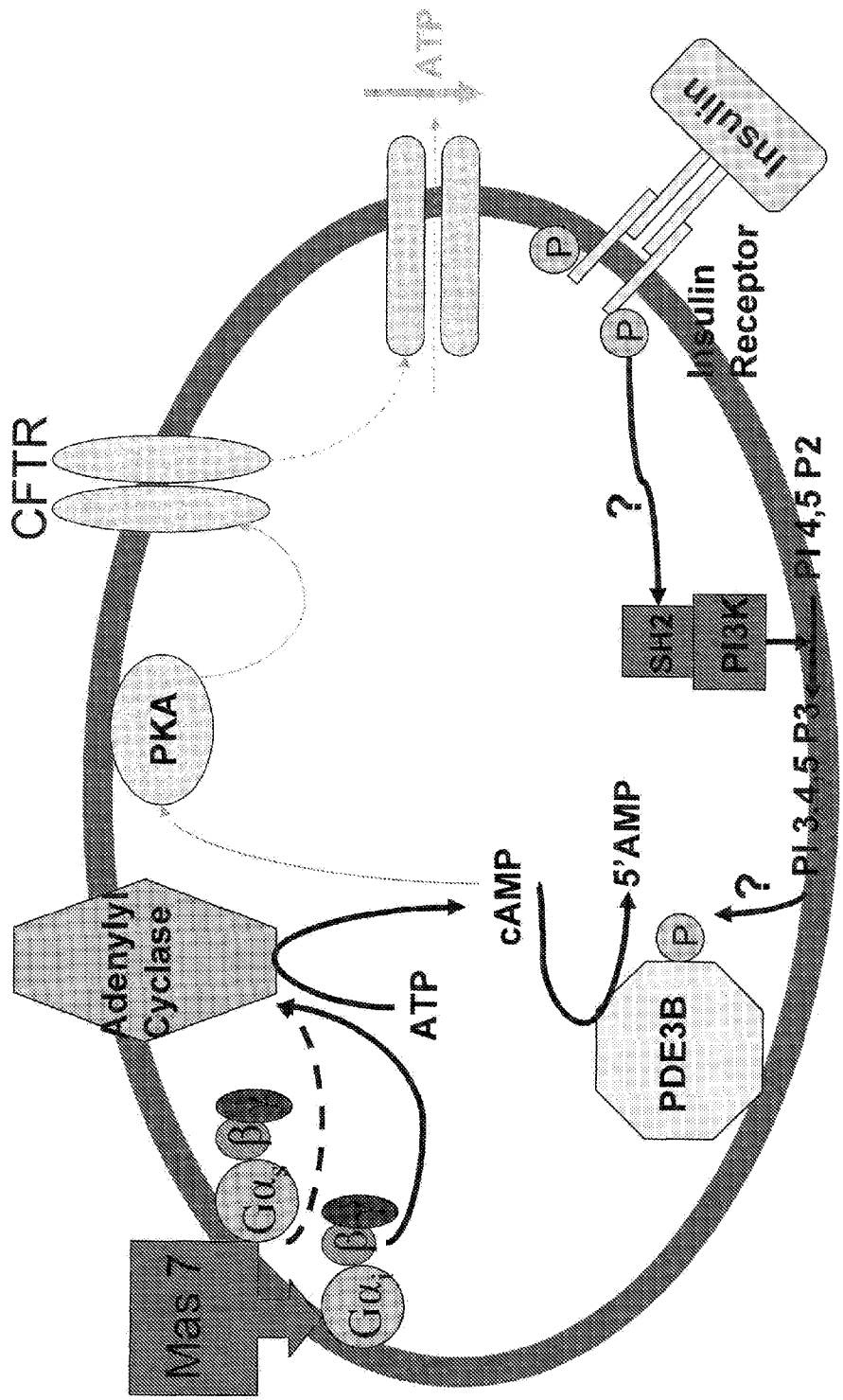
FIG. 10 depicts a cartoon red blood cell and the cell signaling pathway involved in ATP release from the red blood cell, with the novel addition of phosphodiesterase 3B and the insulin receptor.

The oxygen (O2) required to meet the metabolic needs of all tissues is delivered by the erythrocyte, a small, flexible cell containing hemoglobin which, in mammals, is devoid of a nucleus and mitochondria. Recently, it has been demonstrated that this cell is significantly more than an O2 transporter, but rather is a complex cell that controls its own distribution within the microcirculation via its ability to release adenosine triphosphate (ATP) in response to reduced O2 tension [1-5]. Erythrocyte-derived ATP stimulates the synthesis of endothelium-derived vasodilators resulting in increases in blood flow, and, thereby, erythrocyte (O2) supply rate permitting this cell to deliver oxygen in amounts required to precisely meet local metabolic need [5-8]. A signal-transduction pathway that relates ATP release to physiological and pharmacological stimuli has been defined and includes the heterotrimeric G proteins Gs and Gi, adenylyl cyclase (AC), protein kinase A (PKA), and the cystic fibrosis transmembrane conductance regulator (CFTR) (FIG. 10) [9-13]. Importantly, increases in cyclic adenosine monophophate (cAMP) are required for ATP release from erythrocytes suggesting that regulation of the concentration of cAMP could be a critical control point in this pathway [11, 12].

Figure 1:
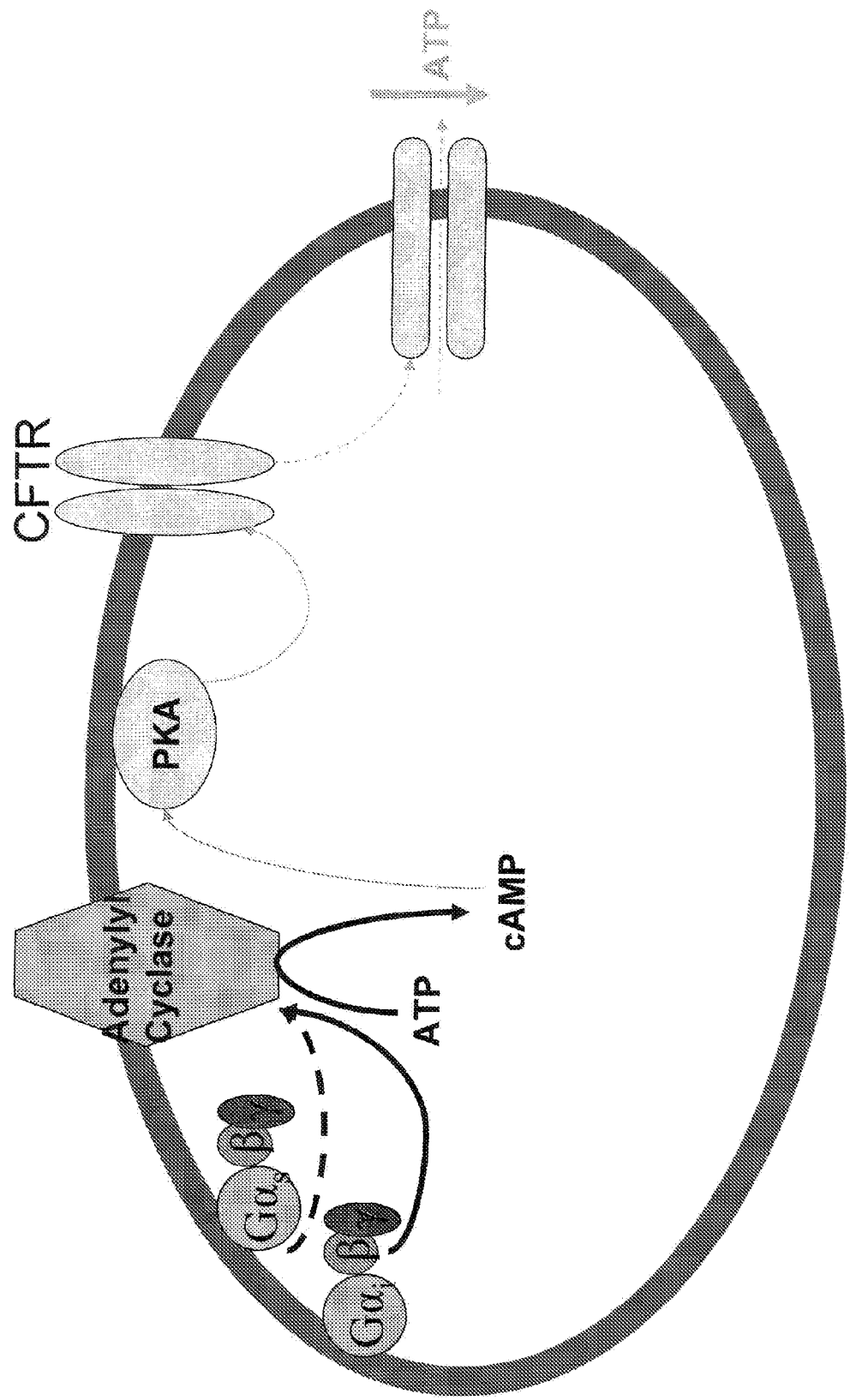
FIG. 1 depicts a cartoon red blood cell and the cell signaling pathway involved in ATP release from the red blood cell.
Figure 2:
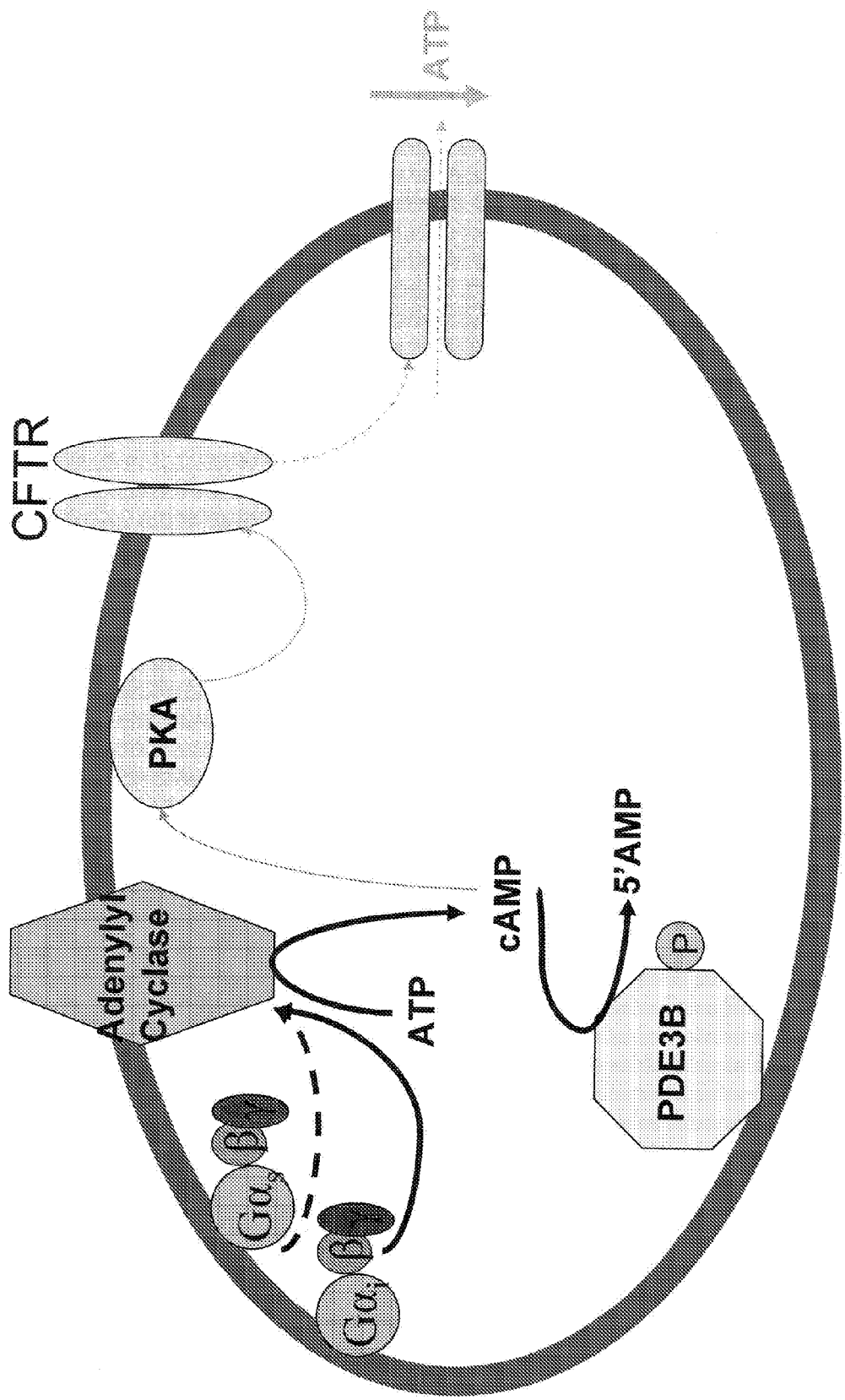
FIG. 2 depicts a cartoon red blood cell and the cell signaling pathway involved in ATP release from the red blood cell, with the novel addition of phosphodiesterase 3B.

In the vasculature of skeletal muscle, failure of the erythrocyte to release ATP in response to reduced O2 tension could be expected to lead to impaired matching of O2 delivery with metabolic need and, thereby, contribute to vascular disease. In support of this hypothesis, the inventors have discovered that ATP release from erythrocytes of humans with type II diabetes is impaired [14], suggesting that this defect in erythrocyte physiology could contribute to the associated vascular disease. It has been reported that vascular complications of type II diabetes are present before diagnosis [15], i.e., during the prediabetic period when normal blood glucose levels are maintained at the expense of marked hyperinsulinemia [16]. It has been previously demonstrated that in prediabetes, increased plasma insulin levels correlate with the degree of microvascular dysfunction, supporting a connection between increased insulin levels and the development of vascular disease [17, 18]. In several tissues, insulin has been shown to activate a signaling pathway involving PI3 kinase (PI3K) that activates phosphodiesterase 3 (PDE3) to hydrolyze cAMP [19-23]. In the erythrocyte, increased hydrolysis of cAMP would impair ATP release in response to physiological stimuli such as exposure to reduced O2 tension as well as in response to pharmacological stimuli (FIG. 1). Human erythrocytes possess insulin receptors and PI3K [24-27], however, neither insulin signaling pathways nor PDE activity in the erythrocyte have been fully characterized.

The inventors herein describe a discovery in which levels of insulin of the magnitude found in humans with prediabetes can activate PDE3 in human erythrocytes resulting in reduced cAMP accumulation and decreased ATP release in response to physiological and pharmacological stimuli [28, 29]. Moreover, while not wishing to be bound by theory, the inventors reasonably postulate that these effects of insulin are the result of receptor-mediated activation of insulin signaling pathways in the erythrocyte and that the adverse effects of insulin can be attenuated by PDE3 inhibition providing a new rational for the use of PDE3 inhibitors in diabetic vascular disease. The inventors have demonstrated that (1) insulin decreases cAMP accumulation in human erythrocytes and, consequently, attenuates ATP release in response to activation of the heterotrimeric G protein Gi as well as the physiological stimulus of exposure to reduced O2 tension, (2) insulin-induced inhibition of erythrocyte cAMP accumulation and ATP release is mediated via activation of the insulin receptor resulting in the stimulation of a signaling pathway involving PI3K/PKB and, ultimately, activation of PDE3, and (3) inhibition of the activity of PDE3 attenuates insulin-induced decreases in cAMP accumulation and ATP release from human erythrocytes in response to physiological and pharmacological stimuli.

Phosphodisesterase isoenzymes (PDEs) are present in every mammalian cell and at least 11 families of PDEs, some with multiple isozymes, have been described [33]. Different PDE families hydrolyze cAMP, cyclic guanosine monophosphate (cGMP) or both cyclic nucleotides [33]. One of these families, PDE3, comprising PDE3A and PDE3B, has been found to be important in regulating such diverse effects of cAMP as lipolysis in adipocytes, glycogen metabolism in liver, apoptosis of cardiomyocytes, aggregation of platelets, and insulin release by β cells [23, 33, 39-42]. Interestingly, insulin, acting through the insulin receptor and associated signaling, has been shown to activate PDE3 in adipocytes enabling insulin to antagonize the effects of cAMP in this cell. The signaling pathway for insulin-induced PDE3 activation requires the tyrosine kinase activity of the insulin receptor, phosphoinositide 3-kinase (PI3K), phosphoinositide-dependent kinases (PDKs), and protein kinase B (PKB) which ultimately phosphorylates serine residues on PDE3B resulting in its activation [20-22, 43-45].

Human erythrocytes possess insulin receptors and have been used to characterize insulin receptor structure and binding characteristics [25, 26, 46, 47]. Although tyrosine kinase activity is present in erythrocytes [48], insulin signaling in this cell has not be studied. Erythrocytes do not require insulin for glucose uptake. However, insulin has been reported to increase calcium flux [49], possibly reflecting insulin signaling in that cell. No studies have addressed the effect of insulin on erythrocyte cAMP levels or ATP release. If insulin signaling does occur in the erythrocyte, one consequence could be the activation of PDE3 leading to increased hydrolysis of intracellular cAMP and inhibition of ATP release in response to physiological and pharmacological stimuli. The inventors have discovered and disclose herein that there is an insulin-mediated effect on ATP release.

In addition to insulin receptors, erythrocytes possess receptors for insulin-like growth factor type 1 (IGF-1) to which insulin binds with low affinity [50, 51]. Additionally, the IGF-1 receptor on β cells has been demonstrated to activate PDE3B [23, 52]. The binding of insulin to either receptor could result in activation of PI3K and, consequently, PDE3B [50]. Importantly, in human erythrocytes, insulin receptors are present in vastly greater numbers that are IGF-1 receptors [24, 46, 51, 53] suggesting that any receptor-mediated effect of effect of insulin is mediated via the insulin receptor.

In humans with prediabetes, high insulin levels maintain normal blood glucose levels during the initial development of insulin resistance [16]. Importantly, microvascular dysfunction in these individuals correlates with plasma insulin levels [17, 18], suggesting a potential pathophysiological consequence of sustained increases in plasma insulin. One reasonably expected consequence of the increased plasma insulin levels in prediabetes could be increased activation of PDE3 within the erythrocyte resulting in enhanced cAMP hydrolysis and, consequently, decreased ATP release in response to exposure to reduced O2 tension. Thus, hyperinsulinemia, via this mechanism, could contribute to the failure to match O2 delivery with metabolic need in the skeletal muscle microcirculation and contribute to the vascular complications of prediabetes. In this disclosure, the inventors determined that insulin, acting through receptor-mediated insulin signaling, activates (in some way, as determined via PDE inhibition) PDE3, leading to decreased cAMP levels and impaired ATP release from erythrocytes in response to exposure to reduced O2 tension as well as in response to pharmacological activation of the heterotrimeric G proteins Gs and Gi.

If insulin-induced activation of PDE3 and subsequent hydrolysis of cAMP is an important contributor to abnormal erythrocyte physiology, it is reasonable to assume that pharmacological agents that decrease PDE3 activity could hold promise as therapeutic agents for the microvascular disease associated with hyperinsulinemia, and type 2 diabetes. Currently, an agent that is a relatively selective PDE3 inhibitor, cilostazol, is approved for use in the treatment of intermittent claudication [54], a condition in which O2 supply to skeletal muscle is inadequate to meet metabolic need. However, the mechanism by which cilostazol improves the symptoms of claudication has not been defined. The inventors herein establish and disclose that inhibitors of PDE3 activity increase cAMP levels in erythrocytes and facilitate ATP release in response pharmacological mediators as well as exposure of erythrocytes to reduced O2 tension. This important and useful discovery provides a heretofore novel mechanism of action of PDE3 inhibitors used clinically in vascular disease and suggests a new indication for these agents in the treatment of the microvascular disease of diabetes. Thus, the invention is directed to compositions (PDE3 inhibitors, direct and indirect) and methods of treating microvascular disease, by employing a PDE3 inhibitor in a pharmaceutically acceptable incipient.

It is important to recognize that, in the study of the mature erythrocyte, the use of many molecular tools is precluded. Erythrocytes lack a nucleus and protein synthesis capability. Thus, in yet another embodiment, the inventors have developed an experimental approach (kits, tools and process) that utilizes physiological stimuli as well as traditional pharmacological approaches coupled with activity assays and Western analysis of erythrocyte membrane fractions to investigate the role of PDE3 and its regulation by insulin and pharmacological agents in ATP release from erythrocytes. These methods are exemplified in the examples that follow.

Example 1

PDE3 in RBCs and the Effect of Insulin on ATP Release by RBCs

Erythrocytes possess the heterotrimeric G proteins Gi and Gs as well as adenylyl cyclase. Importantly, activation of either of these G proteins results in stimulation of adenylyl cyclase and the synthesis of cAMP. Increases in cAMP are required for ATP release from erythrocytes. ATP released from erythrocytes in the vascular lumen is a stimulus for nitric oxide synthesis. Incubation of erythrocytes with Mastoparan 7, a compound that activates Gi, results in increases in cAMP and ATP release (Am. J. Physiol. Heart Circ. Physiol. 287(2): H748-H754, 2004, which is herein incorporated by reference.) The concentration of cAMP in cells is dependent on the rate of its synthesis as well as its degradation by phosphodiesterases (PDEs). Previous studies demonstrate that PDE3 activity is increased by insulin and inhibited by cilostazol in a number of cell types (Cell. Signal. 7(5): 445-455, 1995). Erythrocytes have a well characterized insulin receptor; however, it has not been determined if the mature erythrocyte possesses PDE3. Here, we investigate the hypothesis that human erythrocytes possess PDE3 and that insulin decreases intracellular cAMP, thereby inhibiting ATP release from these cells.

Isolation of Human Erythrocytes

Human blood was obtained by venipuncture. Blood (35 ml) was collected in a syringe containing heparin (500 units) and centrifuged at 500×g for 10 min at 4° C. The plasma, buffy coat, and uppermost erythrocytes were removed by aspiration and discarded. The remaining erythrocytes were washed three times in buffer (in mM; 21.0 Tris-HCl, 4.7 KCl, 2.0 CaCl2, 140.5 NaCl, 1.2 MgSO4 with 2.5% dextrose and 0.5% bovine serum albumin, fraction V, final pH adjusted to 7.4). After the last centrifugation, the hematocrit of the erythrocytes was determined. The protocol for blood collection was approved by the Institutional Review Committee of Saint Louis University.

Incubation of Erythrocytes with Pharmacological Agents

Erythrocytes (20% hct) were incubated with Mastoparan 7 (10 µM) or its vehicle in the presence or absence of 1 uM insulin. ATP release from erythrocytes was measured at 5 minute intervals using the luciferan/luciferase assay. In separate studies, erythrocytes (50% hct) were incubated with vehicle, 10 uM cilostazol, 100 µM cilostazol, 1 insulin, 3 uM insulin, and/or 10 uM Mastoparan 7 for determination of cAMP concentration. At timed intervals, 4 mL of ice cold ethanol containing 1 mM HCl was added to 1 mL of RBC suspension. After centrifugation at 14,000×g at 4° C. for 10 min., the supernatant was dried under vacuum. Samples were resuspended in assay buffer and cAMP concentration was determined in duplicate by EIA.

Western Blot Analysis

Erythrocyte membranes were prepared by lysis of erythrocytes in buffer containing 5 mM Tris-HCl and 2 mM EDTA with pH adjusted to 7.4. Erythrocyte membranes were then isolated by centrifugation at 23,700×g at 4° C. for 10 min. Protein concentration in the pellet was determined by BCA assay. Membrane proteins were solubilized in SDS sample buffer (8% SDS, 60% glycerol, 0.25 M Tris HCl (pH 6.8), 0.004% bromophenol blue, and 400 mM dithiothreitol) and boiled for 5 min before loading onto a 5% gel. After electrophoresis, proteins were transferred onto a PVDF membrane in buffer containing 25 mM Tris-base, 192 mM glycine, and 10% methanol. The PVDF membranes were then blocked overnight with 5% non-fat dry milk in phosphate-buffered saline containing 0.1% Tween-20. Membranes were immunoblotted with an antibody directed against amino acids 1-300 of human PDE3B. Membranes were then incubated with donkey anti-rabbit IgG-horseradish peroxidase and protein was visualized using enhanced chemiluminesence.

Data Analysis

Values are mean±SEM. Statistical significance was determined by ANOVA followed by Fisher's LSD or paired T-test, as appropriate.

Summary

PDE3B has been identified, for the first time, in the membrane of human erythrocytes. In the presence of cilostazol, a phosphodiesterase 3 inhibitor, basal cAMP levels are increased in human erythrocytes. Mastoparan 7, compound that activates Gi, results in cAMP production and ATP release from human erythrocytes. Incubation of erythrocytes with insulin results in decreases in both Mas7-induced cAMP accumulation and ATP release.

Conclusion

These findings support previous studies demonstrating that Mastoparan 7, by activating Gi in the human erythrocyte, stimulates adenylyl cyclase resulting in increased cAMP production and ATP release from these cells. Release of ATP has been suggested to be an important factor in matching blood flow with metabolic need in skeletal muscle. In the work presented here we show that, in human erythrocytes, insulin reduces both cAMP production and ATP release in response to Mastoparan 7. These findings are consistent with the hypothesis that PDE3B, present in human erythrocytes, can be activated by insulin. One interpretation of these results is that increased plasma insulin could contribute to the vascular complications of diabetes. We postulate that this effect of insulin is modulated via the following signal transduction pathway.

Example 2

Insulin decreases cAMP accumulation in human erythrocytes and, consequently, attenuates ATP release in response to exposure to reduced O2 tension as well as pharmacological activation of the heterotrimeric G proteins Gs and Gi. Incubation of erythrocytes of humans with mastoparan 7 (MAS7), a direct activator of Gi, results in cAMP accumulation and ATP release [10, 12]. In other cells, insulin has been has been shown to decrease cAMP levels, a requisite for erythrocyte ATP release, by activating phosphodiesterase 3 (PDE3) [20, 23].

Figure 8:
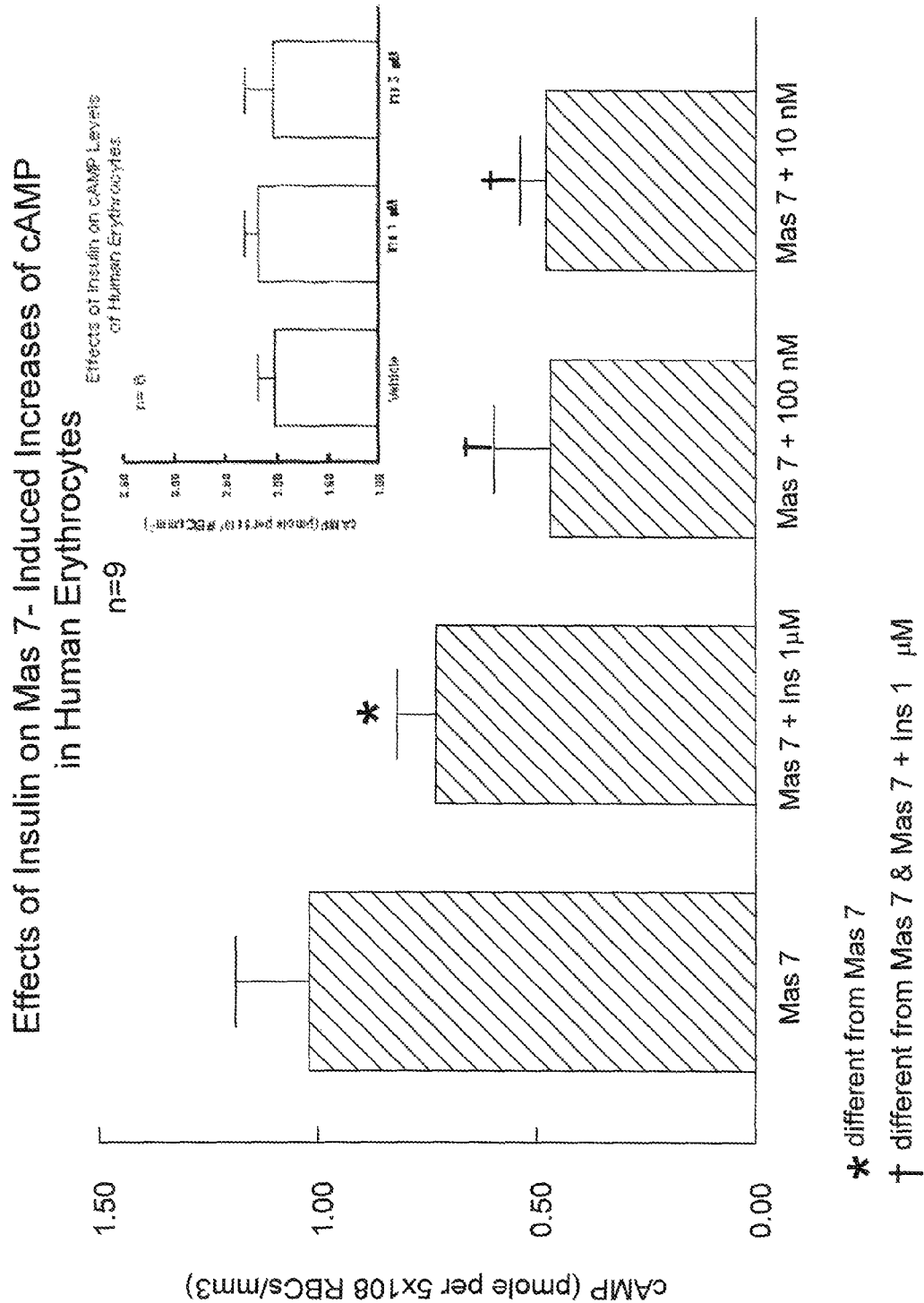
FIG. 8 depicts cAMP produced by RBCs treated with insulin. Insulin reduces the amount of cAMP produced by RBCs under Mas7 (Gi) stimulation.
Figure 9:
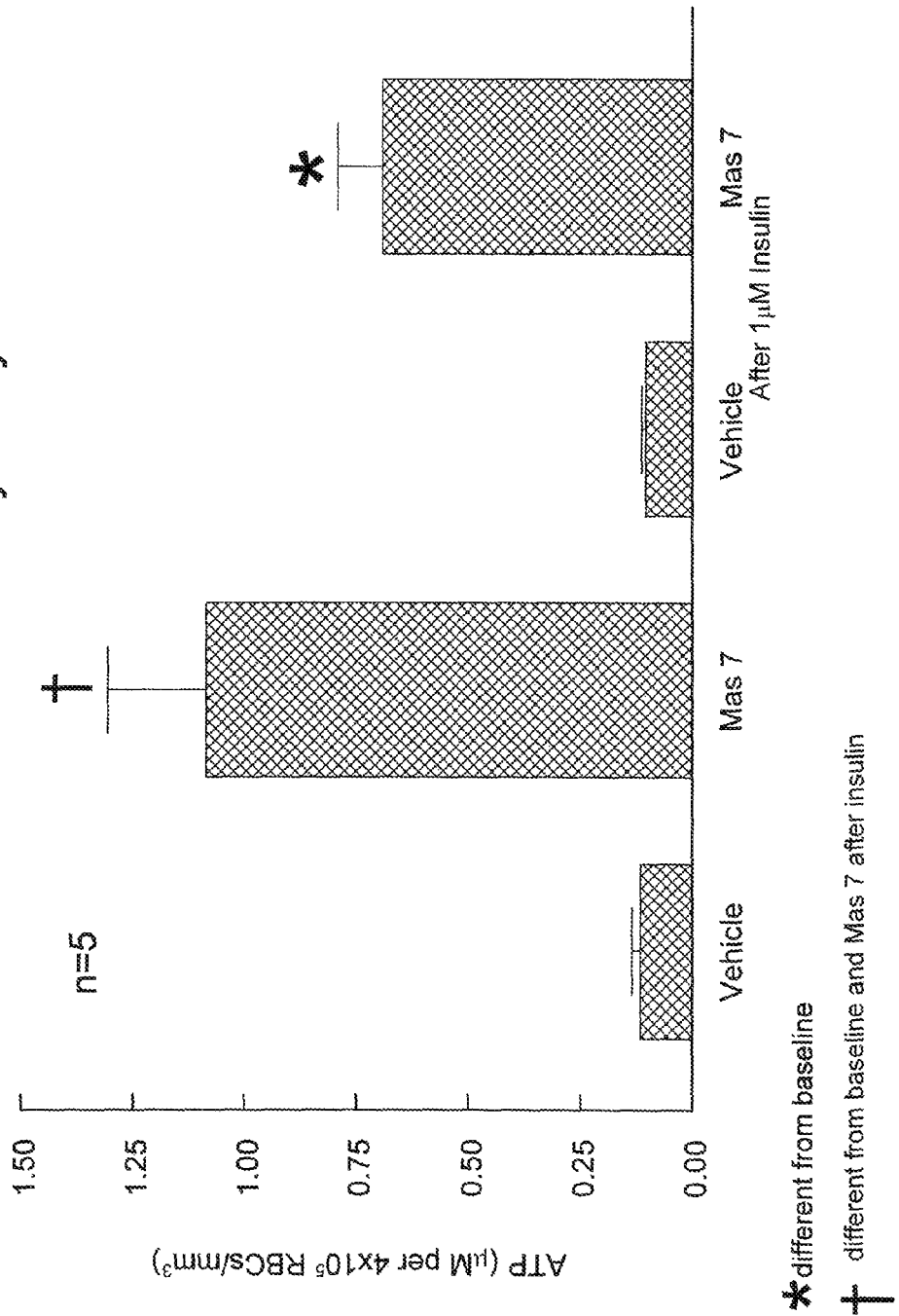
FIG. 9 depicts ATP released by RBCs treated with insulin. Insulin reduces the amount of ATP released by RBCs under Mas7 (Gi) stimulation.

The inventors have shown that pre-incubation of human erythrocytes with insulin (1 µM) attenuated MAS7 (10 µM)-induced ATP release in the absence of changes in total ATP content (FIG. 9, Example 1). Importantly, insulin pre-treatment also resulted in inhibition of MAS7 (10 µM)-induced cAMP accumulation (FIG. 8, Example 1). These results provide support for the hypothesis that insulin, at concentrations present in humans with pre-diabetes, inhibits cAMP accumulation, a requisite for ATP release from erythrocytes, possibly via stimulation of cAMP hydrolysis [28, 29].

Protocol A: Washed erythrocytes are incubated with insulin (0.1 nM-1 µM, Humalog®), or its vehicle (saline) for 30 min [28, 29, 47, 60]. Erythrocytes are incubated with either iloprost (1 µM), isoproterenol (10 µM) (receptor-mediated activators of Gs) or mastoparan 7 (MAS7, 10 µM) (a direct activator of Gi) or their vehicle (saline) [9, 10, 12, 57, 61]. After 15 min, cAMP accumulation and ATP release will be determined.

For controls: Humalog® is a human insulin analog with the reversal of the position of two amino acid residues at the C terminal of the B chain. This modification results in an insulin that displays a decreased tendency to dimerize and therefore retains its activity under in vitro conditions. Still, Humalog® is equipotent to human insulin on a molar basis (product insert, Eli Lilly) Under all protocols, a limited number of identical experiments are conducted using regular human insulin (Humulin®, Eli Lilly) in lieu of Humalog® to establish that any effect of Humalog® is not the result of this structural alteration. Finally, total intracellular ATP and free hemoglobin, a measure of erythrocyte lysis, are determined (infra).

Protocol B: To determine the effects of insulin on erythrocyte cAMP accumulation and ATP release induced by decreased O2 tension, washed erythrocytes are incubated with insulin (0.1 nM-1 µM) or its vehicle (saline) for 30 min. Erythrocytes are then placed in a tonometer (infra) and exposed to gas containing 15% O2, 5% CO2; 0% O2, 5% CO2, (normoxia, pO2≈100 mm Hg). The pH, pCO2 and pO2 as well as cAMP or ATP concentration are determined at 30 min. after addition of the erythrocyte suspension to the tonometer. The gas tension will then be changed to 4.5% O2, 5% CO2; 0% O2, 5% CO2, (hypoxia, pO2≈20 mm Hg) and pH, gas tensions, cAMP and ATP measurements are repeated at 5, 10, and 15 min. Finally, the gas tension is returned to the "normoxic" gas composition (recovery) and the measurements are at 30 min.

Protocol C: To determine effects of direct activation of adenylyl cyclase and active cAMP analogs on ATP release from erythrocytes in the presence of insulin, washed erythrocytes are incubated with insulin (0.1 nM-1 µM) or its vehicle (saline). After 30 min, the cells are incubated with either the non-selective activator of adenylyl cyclase (AC) activity, forskolin (1 to 10 µM) [11], or one of two active cAMP analogs that are resistant to degradation, SpcAMP (10 to 100 µM) [11] or 8-bromo-cAMP (10 to 100 µM) [62]. ATP release will be measured at 5, 10 and 15 min after addition of forskolin or the active cAMP analogs. Controls: To ensure the effects of forskolin or the cAMP analogs are not due to effects of vehicle or time, identical experiments are conducted using their vehicles, N,Ndimethylformamide (DMF) or saline, respectively, in lieu of the active agent. Total intracellular ATP and free hemoglobin, a measurement of erythrocyte lysis, is determined.

Results: Pharmacological activation of Gs (iloprost or isoproterenol), as well as pharmacological (MAS7) and physiological (decreased O2 tension) activation of Gi, stimulate cAMP synthesis in and ATP release from human erythrocytes. Pretreatment of erythrocytes with insulin, at concentrations reported to be present in the plasma of humans with prediabetes, inhibited both cAMP accumulation and ATP release from human erythrocytes. These effects of insulin reflect negative cooperative binding of insulin binding with its receptor, i.e., nM concentrations of insulin will be more effective. The findings that insulin inhibits both Gs- and Gi-mediated ATP release but has no effect on ATP release in response to active cAMP analogs that are resistant to hydrolysis by PDEs provides strong support that insulin acts to decrease ATP release via activation of PDE activity in the human erythrocyte and not on other components of the signal transduction pathway (FIG. 1, above).

Example 3

Insulin-induced inhibition of erythrocyte cAMP accumulation and ATP release is mediated via activation of the insulin receptor resulting in the stimulation of a signaling pathway reasonably expected to involve PI3K/PKB and, ultimately, activation of PDE3. Although human erythrocytes have been shown to possess insulin receptors [25, 26, 46, 47], a role in erythrocyte physiology has not been defined. The preliminary results reported above (FIGS. 8, 9) suggest that insulin can inhibit both cAMP accumulation and ATP release from erythrocytes. Importantly, the effect on cAMP accumulation is greater at lower (nM) insulin concentrations (FIG. 8). The latter finding is consistent with the hypothesis that this effect of insulin is receptor mediated. The binding of insulin to its receptor displays negative cooperativity, such that the dissociation rate of insulin accelerates with increased receptor occupancy [55, 56]. The result is that lower concentrations of insulin stimulate a greater response than do higher concentrations [55, 56].

Figure 3:
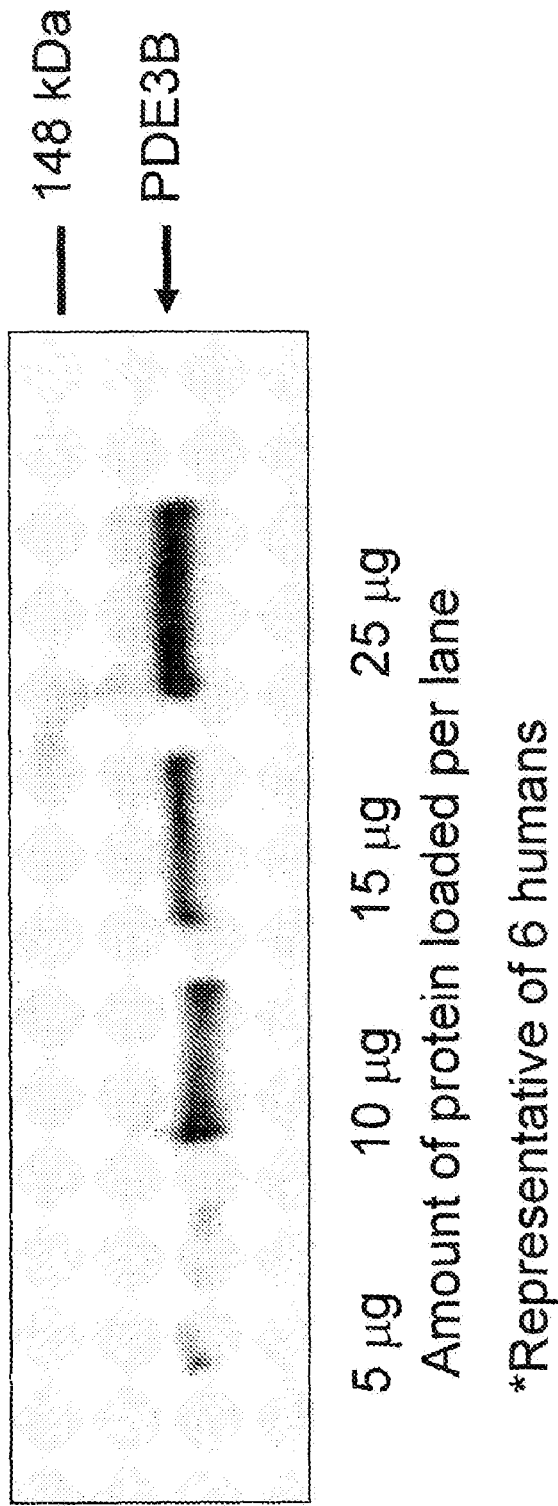
FIG. 3 depicts a portion of a western blot showing PDE3B present in the membranes of human red blood cells.
Figure 4:
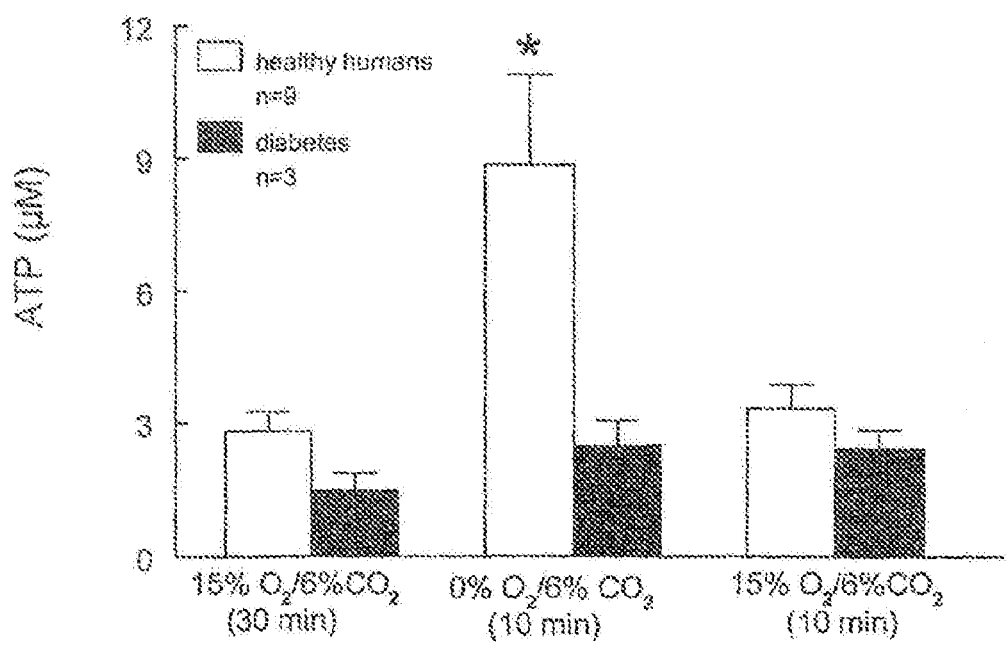
FIG. 4 depicts the release of ATP by RBCs under reduced oxygen tension, showing the reduced ATP release by RBCs from humans suffering from type 2 diabetes.
Figure 5:
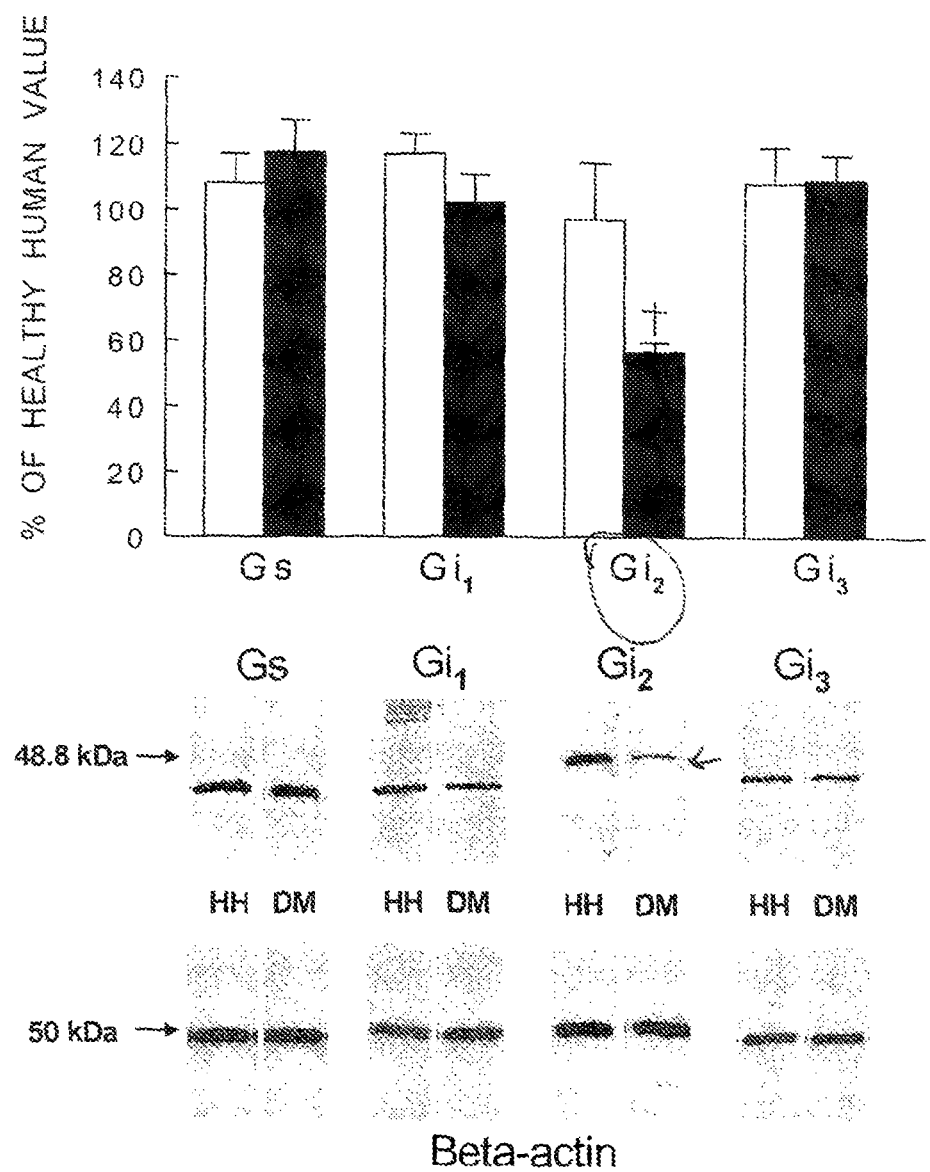
FIG. 5 depicts western blots and quantified data for the expression of various depicted isoforms of G-protein. RBCs from patients suffering from type 2 diabetes show reduced levels of Gi2.
Figure 6:
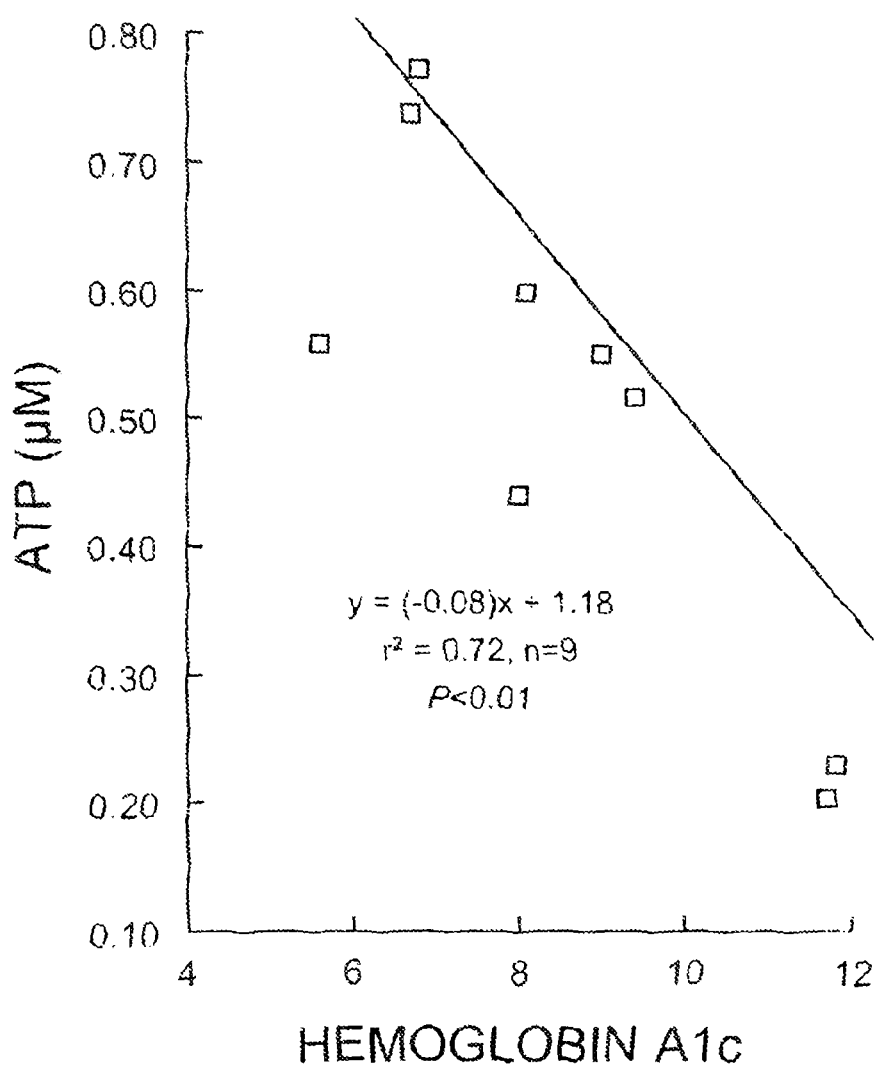
FIG. 6 depicts the amount of RBC released ATP via Mas7 stimulation versus glycosylated hemoglobin, which represents diabetic RBCs. Reduced levels of ATP are released from diabetic RBCs.
Figure 7:
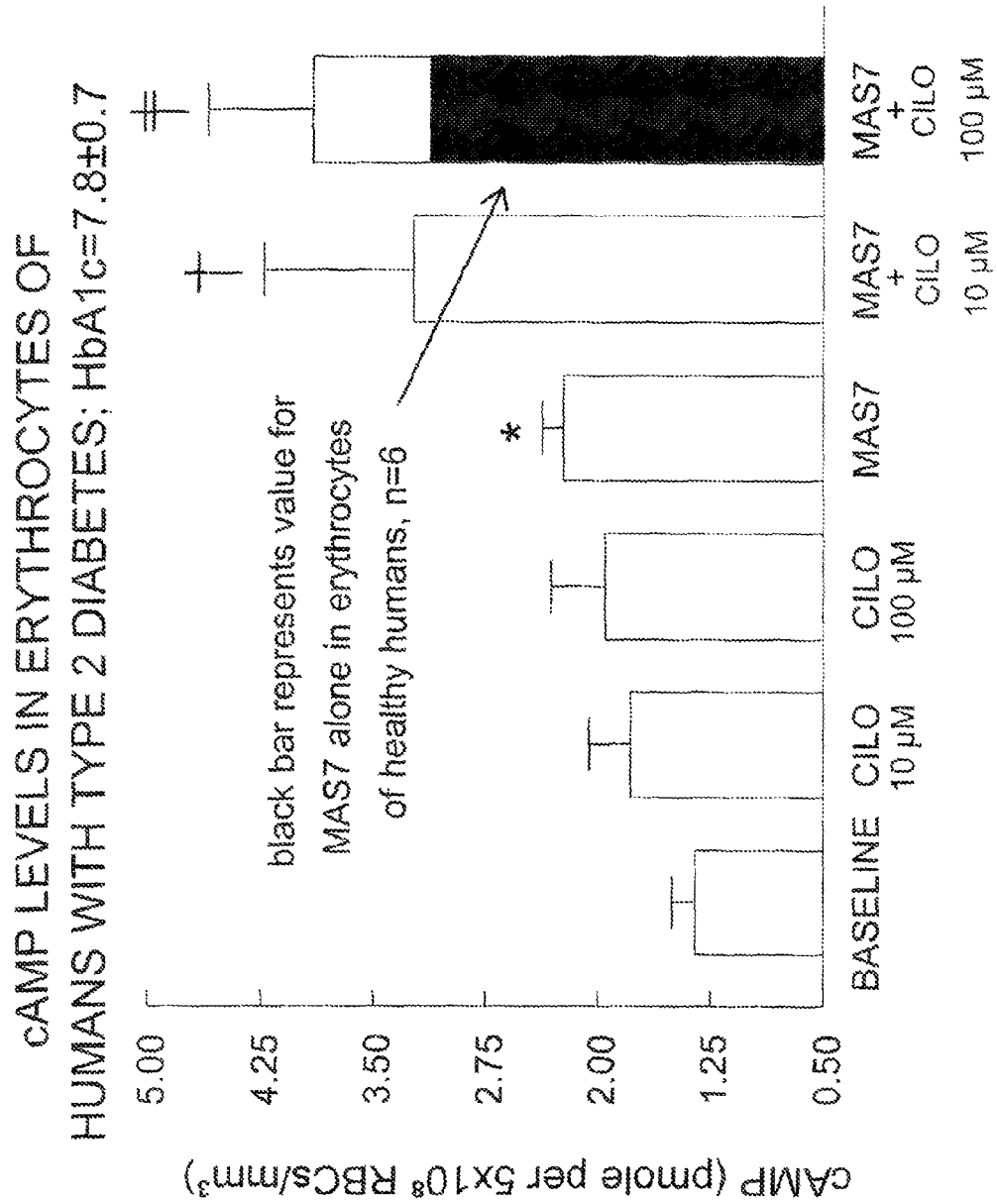
FIG. 7 depicts cAMP levels in type 2 diabetic RBCs stimulated with Mas7. The addition of the PDE3 inhibitor cilostazol enables the diabetic RBCs to release normal levels of ATP under Mas7 stimulation.

Insulin has been reported to produce receptor-mediated activation of PDE3 in other cells resulting in decreases in cAMP [20, 23]. Although PDE activity has been reported in the erythrocyte [34-38], the PDEs involved and the pathways by which they could be regulated have not been characterized. Using Western analysis, we have determined for the first time that PDE3B, the PDE activated by insulin in other cell types [19, 23], is a component of the membranes of human erythrocytes (FIG. 3). Taken together, these preliminary studies are consistent with the hypothesis that inhibition of cAMP accumulation in human erythrocytes by insulin could be mediated via activation of the insulin receptor and subsequent activation of PDE3, a PDE that hydrolyzes cAMP.

In other tissues, insulin antagonizes cAMP action via receptor-mediated activation of signaling pathways that result in activation of PDE3 [20, 22, 23, 45, 52, 65, 66]. Such a signaling pathway has be characterized in adipocytes and includes the insulin receptor, IRS, PI3K, PDKs, PKB, and PP2A [20]. Insulin can interact with two distinct receptors, the insulin receptor and the IGF-1 receptor, both present in erythrocytes membranes and both associated with activation of PDE3 in different cell types [19, 23-25, 46, 50-52].

Protocol A: To determine that tyrosine kinase activity is required for insulin-induced decreases in cAMP accumulation and ATP release in response to physiological and pharmacological stimuli, washed erythrocytes are treated with insulin (0.1 nM-1 µM) or its vehicle (saline) for 30 min followed by the addition of 300 µM hydroxy-2-naphthalenyl-methylphosphonic acid (HNMPA(AM)$_3$), an insulin receptor tyrosine kinase inhibitor [67, 68]. After 30 min, the cells are incubated with either iloprost (1 µM), isoproterenol (10 µM), MAS7 (10 µM) or exposed to reduced O2 tension (supra) and cAMP accumulation and ATP release is determined Control experiments: In separate studies the vehicles for HNMPA-(AM)$_3$, iloprost, isoproterenol and MAS7 (DMF or saline) are used in lieu of the active agent.

Protocol B: To determine the effects of blockade of the IGF-1 receptor on insulin-induced inhibition of cAMP accumulation and ATP release in response to physiological and pharmacological stimuli, washed erythrocytes are treated with a blocking antibody specific for the IGF-1 receptor, αIR3 (1 µg of IgG per 100 µA of erythrocyte suspension for 3 hours) [51], in the presence or absence of insulin (0.1 nM-1 µM). After 30 min, the cells are incubated with either iloprost (1 µM), isoproterenol (10 µM), MAS7 (10 µM) or exposed to reduced O2 tension (as described under Aim 1) and cAMP accumulation and ATP release is determined Control experiments: To ensure the effects of αIR3 are not due to nonspecific effects of the antibody, identical experiments are conducted using pre-immune mouse serum in lieu of αIR3. In addition, experiments with the various vehicles are performed in lieu of the active agents.

Protocol C: To determine the effects of IGF-1 on erythrocyte cAMP accumulation and ATP release in response to physiological and pharmacological stimuli, washed erythrocytes are treated with either IGF-1 (10 µM-100 nM [51]) or its vehicle saline) for 30 min. The cells are then incubated with either iloprost (1 µM), isoproterenol (10 µM), MAS7 (10 µM) or exposed to reduced O2 tension (as described under Aim 1) and cAMP accumulation and ATP release were are determined. In separate studies, erythrocytes are pretreated with αIR3, as described in Protocol A to inhibit any effects of IGF-1 resulting from binding to the IGF-1 receptor. Control experiments: In separate studies the vehicles for IGF-1, iloprost, isoproterenol and MAS7 (DMF or saline) are used in lieu of the active agent.

Protocol D: To establish that the effects of insulin-induced decreases in cAMP accumulation and ATP release are the result of increased activity of the phosphodiesterase, PDE3, erythrocyte membranes are incubated with insulin (0.1 nM-1 µM) or its vehicle (saline) in the absence or presence of the PDE3 selective inhibitors cilostazol (10, 30, or 100 µM) or milrinone (10 or 30 µM) [39, 54, 69]. cAMP substrate is added to the isolated membranes and amounts of hydrolyzed AMP(PDE activity) were determined as described (infra).

The ability of PDE3 inhibitors to interfere with insulin-induced increases in PDE activity is interpreted to mean that insulin activates PDE3 activity in this system. Control experiments: Identical experiments are performed with the vehicle for cilostazol and milrinone, DMF.

Protocol E: To determine that PI3K is required for insulin-induced inhibition of cAMP accumulation and ATP release in response to physiological and pharmacological stimuli, washed erythrocytes are treated with insulin (0.1 nM 1 µM) or its vehicle (saline) for 30 min. Cells are then treated with either of two PI3K inhibitors, LY294002 (1 µM) or wortmannin (100 nM) [22, 27]. After 30 min, the cells are incubated with either iloprost (1 µM), isoproterenol (10 µM), MAS7 (10 µM) or exposed to reduced O2 tension (as described supra) and cAMP accumulation and ATP release are determined Control experiments: In separate studies the vehicle for LY29002 and wortmannin (DMF) are used in lieu of the active compounds.

Protocol F: To determine that PKB is required for insulin-induced inhibition of cAMP accumulation and ATP release in response to physiological and pharmacological stimuli, washed erythrocytes are treated with insulin (0.1 nM-1 µM) or its vehicle (saline) for 30 min in addition to a PKB inhibitor (Akti-½, 1 µM-30 µM) [70]. The cells are then incubated with either iloprost (1 µM), isoproterenol (10 µM), MAS7 (10 µM) or exposed to reduced O2 tension (as described supra) and cAMP accumulation and ATP release are determined Control experiments: In separate studies the vehicle (DMF) for Akti-½ is used in lieu of the active compound.

Results: This example is expected to demonstrate[s] that, in the erythrocyte, insulin-induced inhibition of cAMP accumulation and ATP release is mediated via activation of the insulin receptor. In support of this hypothesis, it is demonstrated that inhibition of tyrosine kinase activity prevents the actions of insulin since this activity is required for the insulin receptor to initiate downstream signaling. It is reasonably expected that blockade of the IGF-1 receptor does not prevent the ability of insulin to inhibit cAMP accumulation and ATP release. The use of the PDE activity helped to establish that the ability of insulin to decrease cAMP accumulation is related to the stimulation of PDE3. Finally, inhibition of either PI3K or PKB is expected to prevent activation of PDE3 by insulin, suggesting that both are components of an insulin signaling pathway for activation of PDE3 in erythrocytes, as has been reported in other cell types. Additional support of a role for PKB was obtained by the demonstration that inhibition of PKB prevents the activation of PDE3 and, thereby potentiates cAMP accumulation and ATP release in response to pharmacological stimuli. Taken together, these experiments are expected to demonstrate that insulin bound to the erythrocyte insulin receptor stimulates the activation of PDE3 in the erythrocyte via a signaling pathway that involves PI3K and PKB.

Example 4

Inhibition of the activity of PDE3 attenuates insulin-induced decreases in cAMP accumulation and ATP release from human erythrocytes in response to physiological and pharmacological stimuli. The inventors had demonstrated that PDE3B is present in erythrocyte membranes (supra). In this example, a role for this PDE in the regulation of cAMP levels in human erythrocytes is demonstrated.

Figure 11:
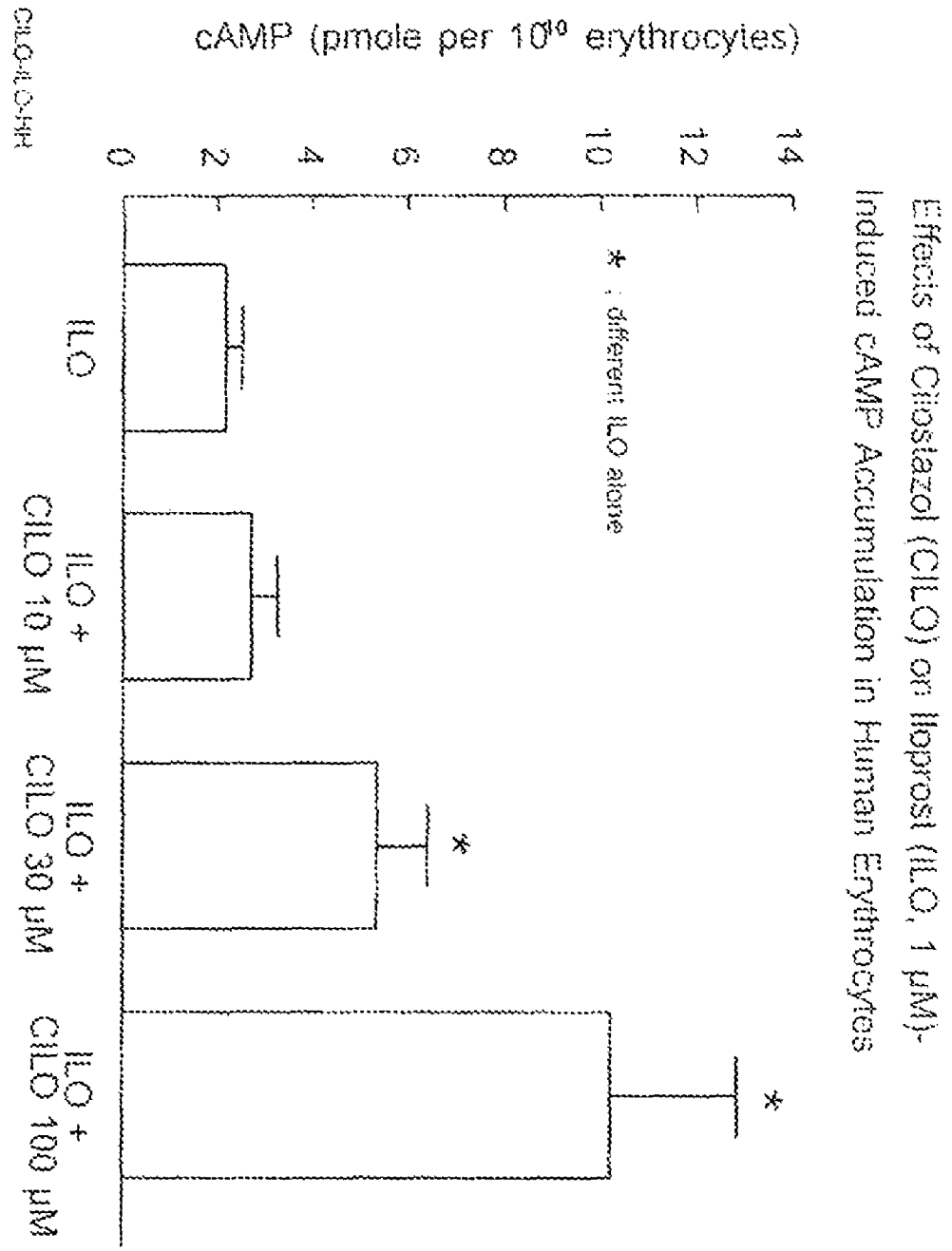
FIG. 11 depicts the effects of cilostazol on iloprost stimulation of cAMP accumulation in human RBCs.
Figure 12:
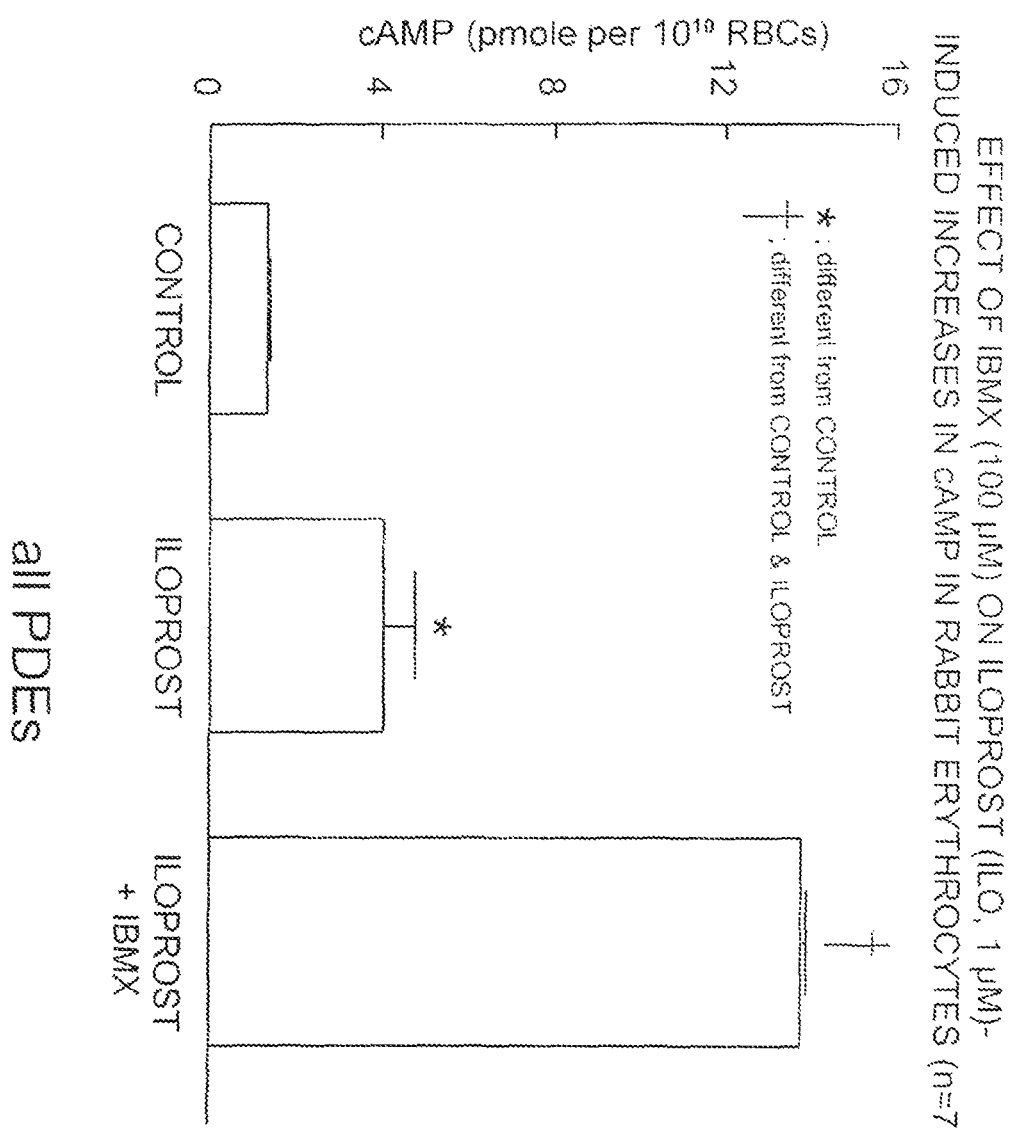
FIG. 12 depicts the effects of IBMX on iloprost stimulation of cAMP accumulation in rabbit RBCs.
Figure 13:
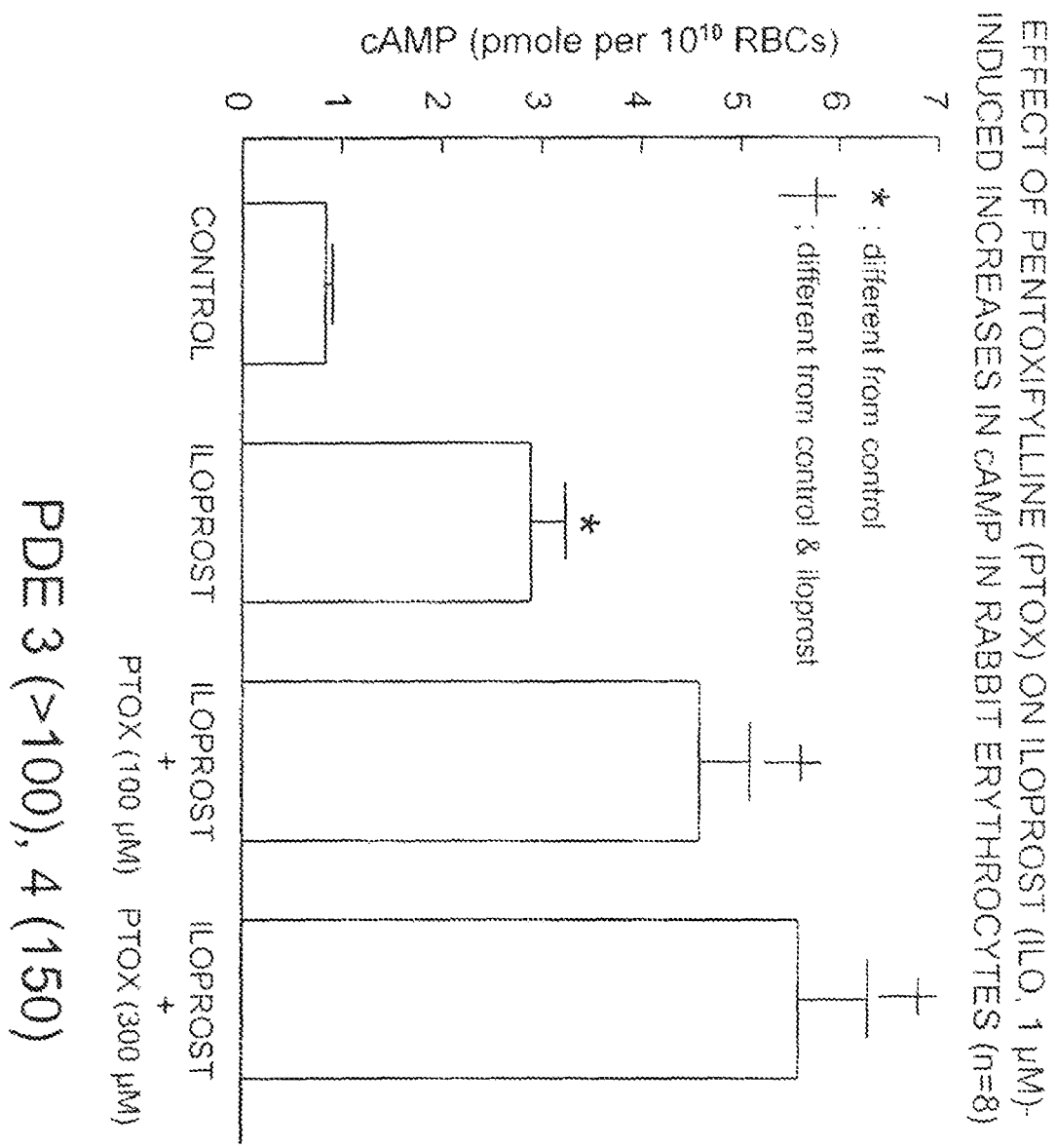
FIG. 13 depicts the effects of pentoxifylline on iloprost stimulation of cAMP accumulation in rabbit RBCs.
Figure 14:
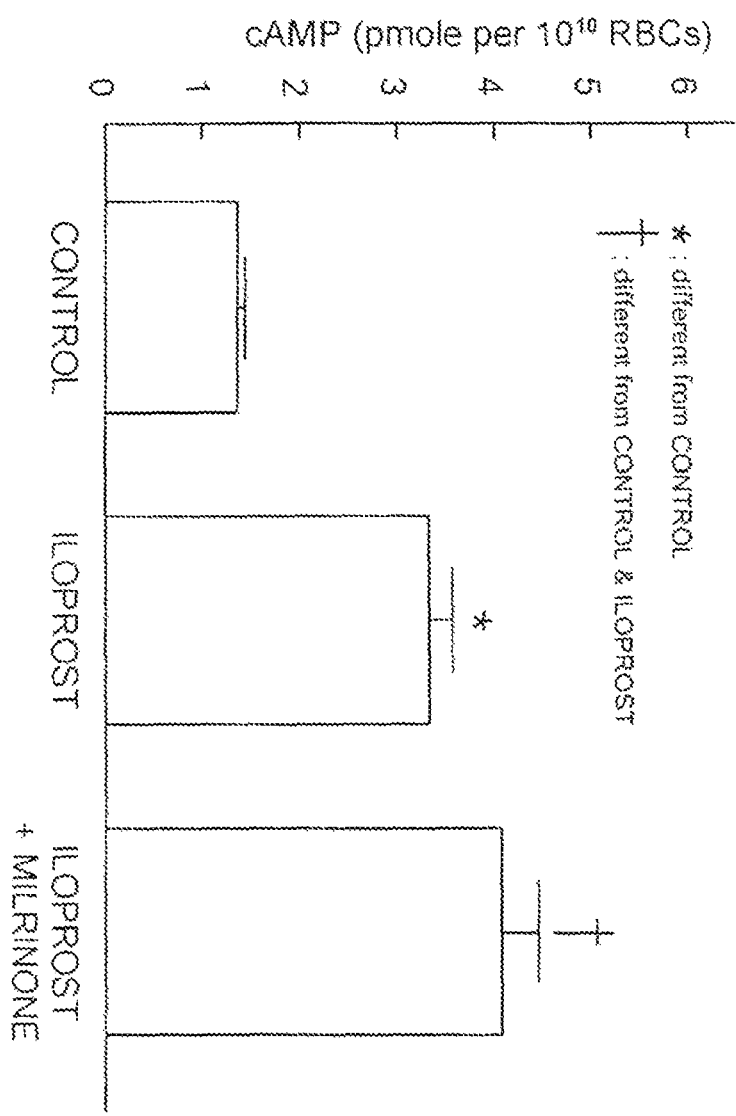
FIG. 14 depicts the effects of milrinone on iloprost stimulation of cAMP accumulation in rabbit RBCs.
Figure 15:
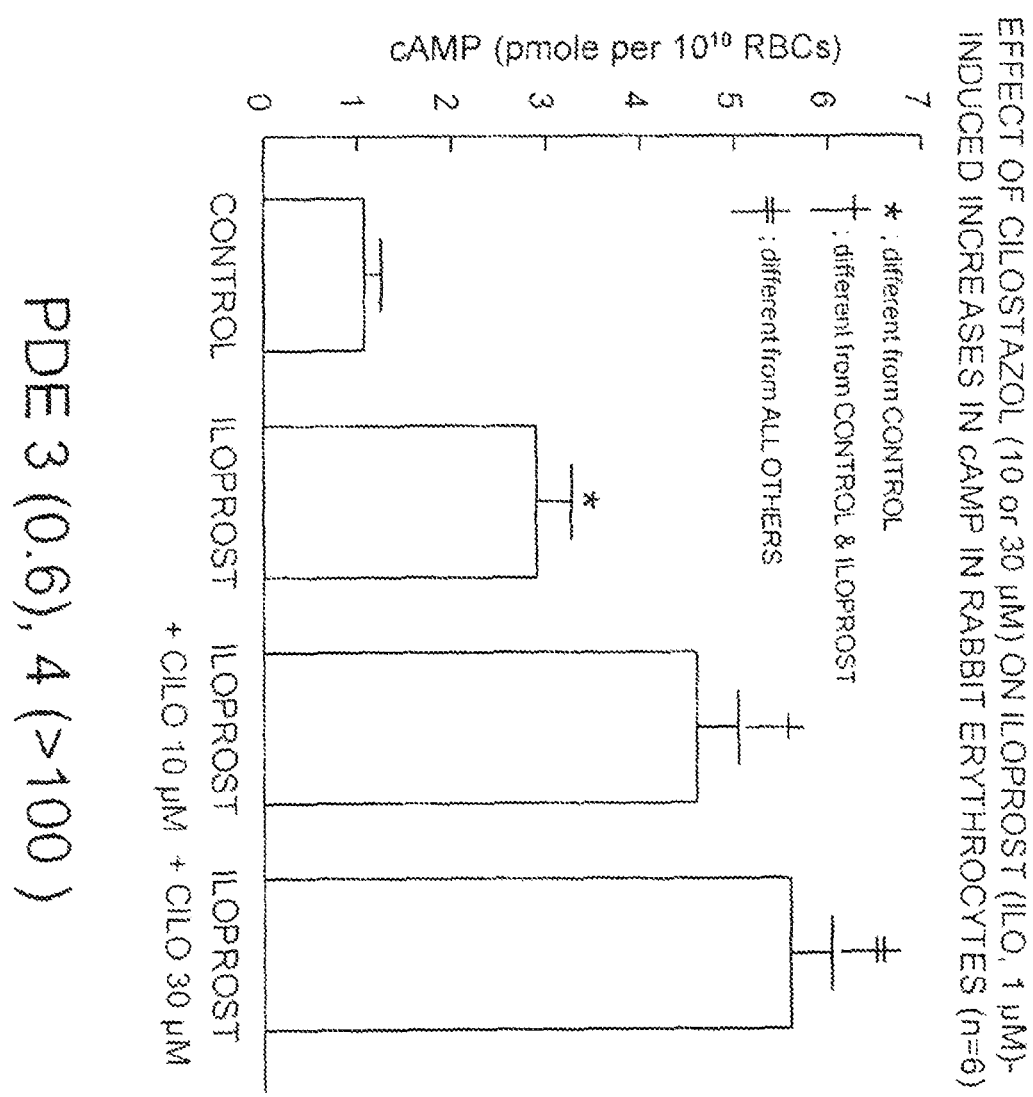
FIG. 15 depicts the effects of cilostozol on iloprost stimulation of cAMP accumulation in rabbit RBCs.

To begin to address this issue, studies were performed in which erythrocytes were pre-incubated with cilostazol, a well characterized inhibitor of PDE3 activity [54], and then exposed to iloprost, a prostacyclin analog that produces receptor-mediated activation of Gs and increases in cAMP in erythrocytes [9, 12, 57]. As depicted in FIG. 11, cilostazol pre-treatment resulted in concentration-dependent increases in iloprost-induced cAMP accumulation. In addition to effects on PDE3, cilostazol has been reported to inhibit PDE4 activity [54], but at concentrations ten-fold greater than those used here. Importantly, the inventors have established that the selective inhibitor of PDE4 activity, rolipram (30 µM, n=6) [33], has no effect on iloprost-induced cAMP accumulation in human erythrocytes suggesting that the effects of cilostazol are the result of selective inhibition of PDE3 activity.

Protocol A: To confirm that the protein identified by Western analysis is PDE3B and that it is present in the erythrocyte membrane, purified erythrocytes membranes were subjected to Western analysis as described in General Methods (infra) using multiple antibodies directed against different epitopes of PDE3B. Control experiments: To establish that membrane preparations are devoid of platelets which contain an isoform of PDE3, the membrane preparations were probed for CD41, a protein found in platelets, but not erythrocytes [40, 72]. In addition, lack of leukocyte contamination was determined by microscopic examination of erythrocyte preparations.

Figure 16:
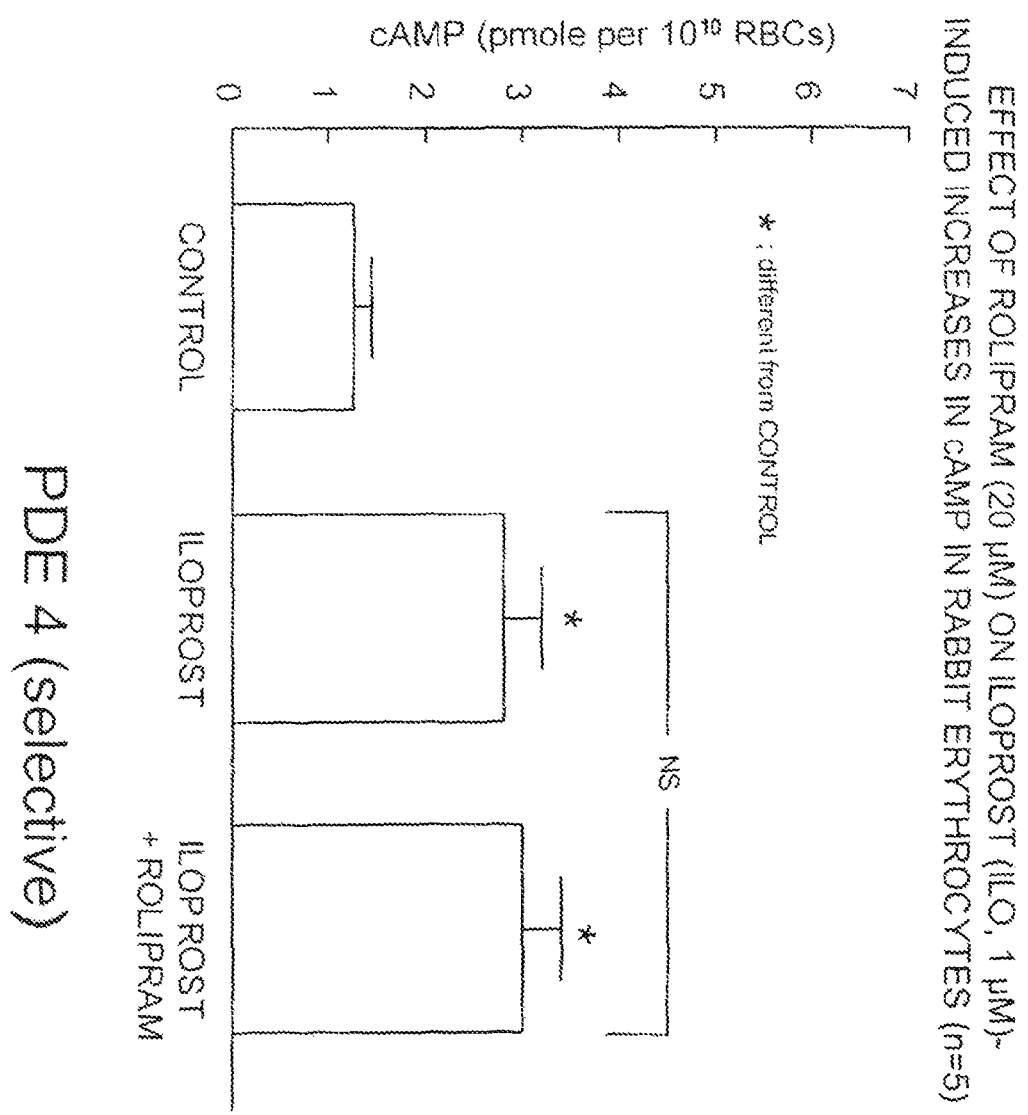
FIG. 16 depicts the effects of rolipram on iloprost stimulation of cAMP accumulation in rabbit RBCs.
Figure 17:
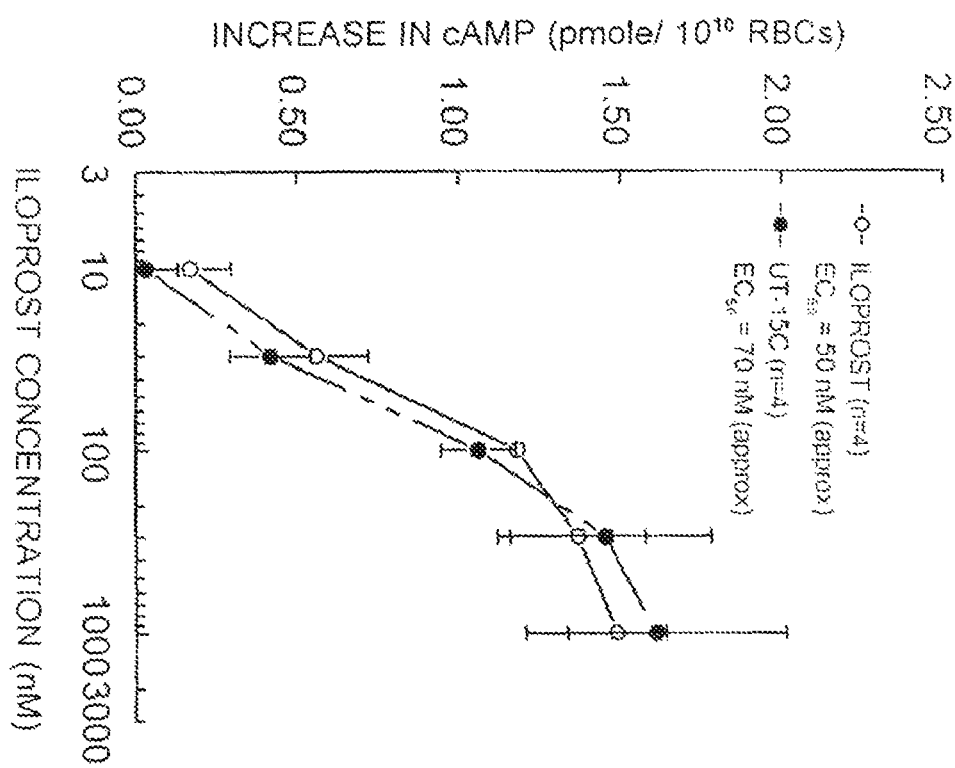
FIG. 17 depicts the effects of the PGI2 analogues iloprost and UT-15C on cAMP accumulation in rabbit RBCs.
Figure 18:
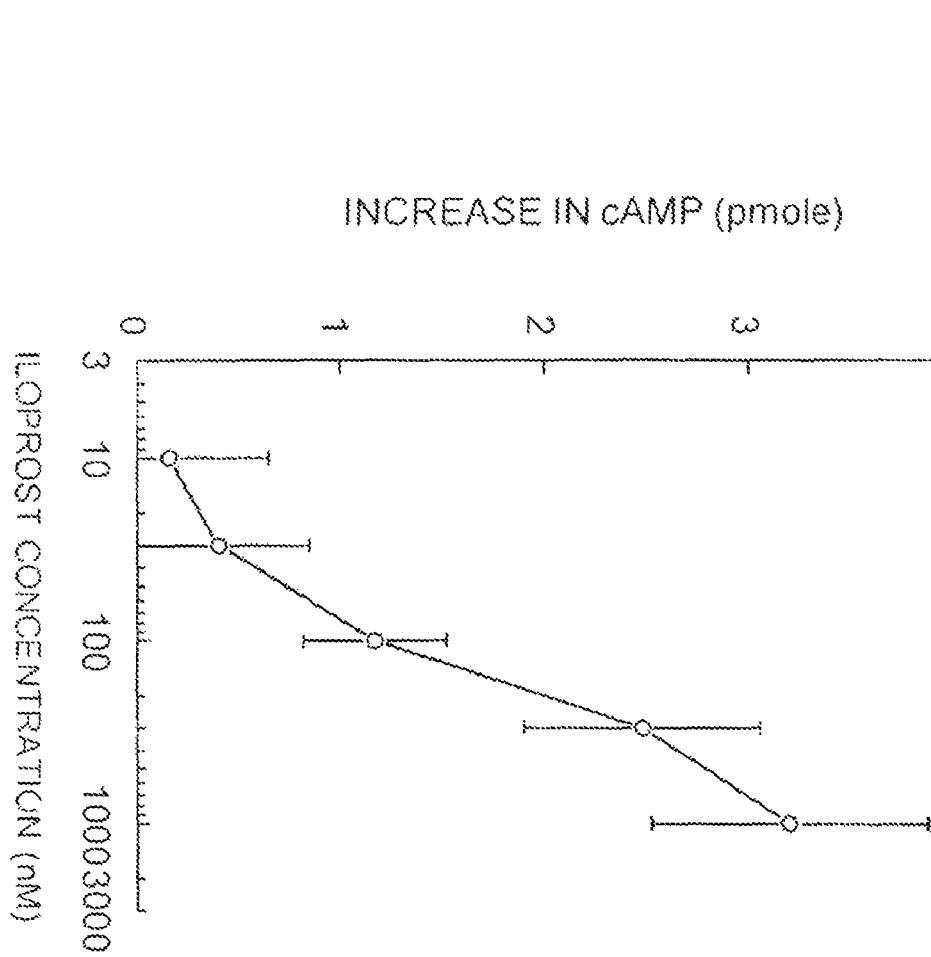
FIG. 18 depicts the effects of the PGI2 analogue iloprost on cAMP accumulation in human RBCs.
Figure 19:
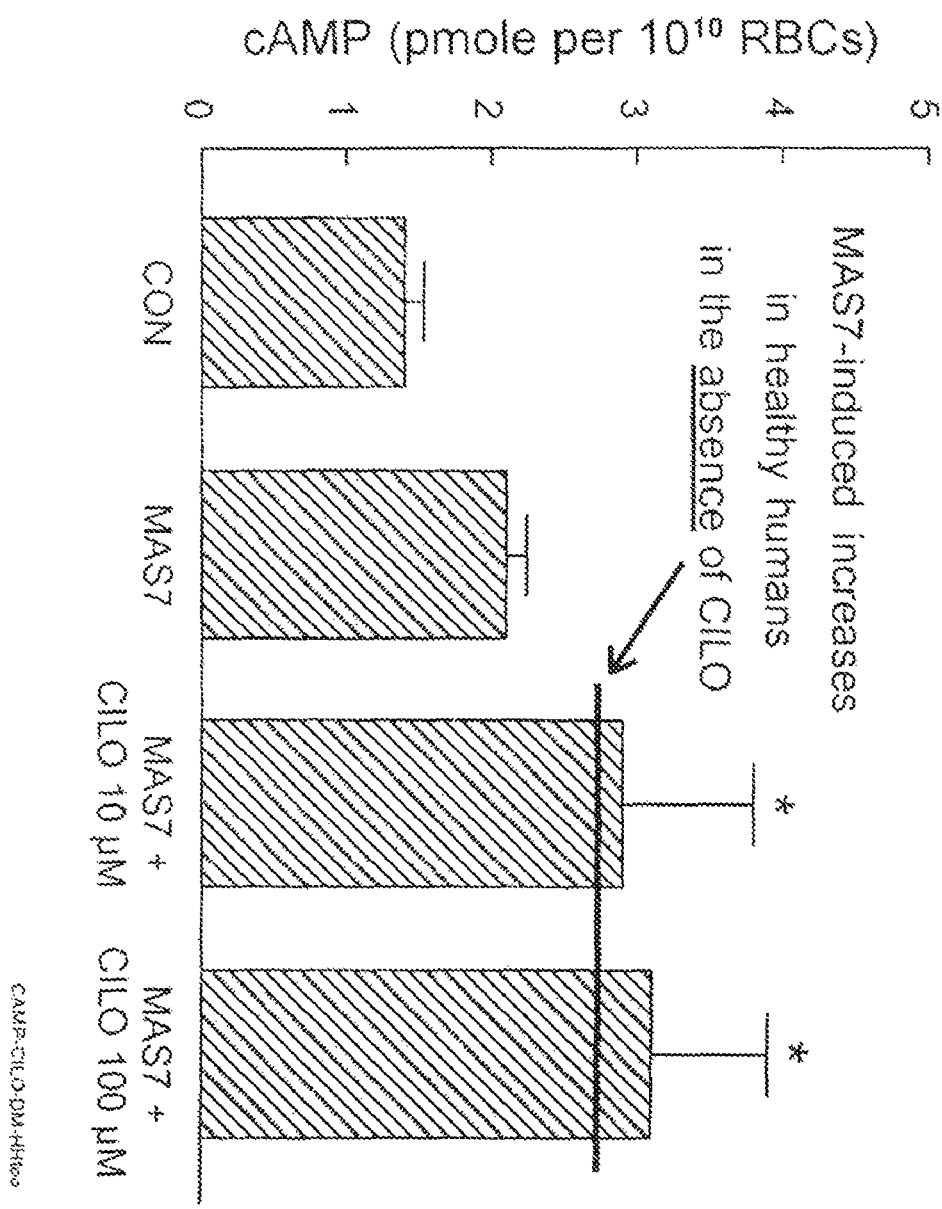
FIG. 19 depicts the effect of cilostazol on Mas7-induced cAMP increases in RBCs derived from humans having type 2 diabetes.
Figure 20:
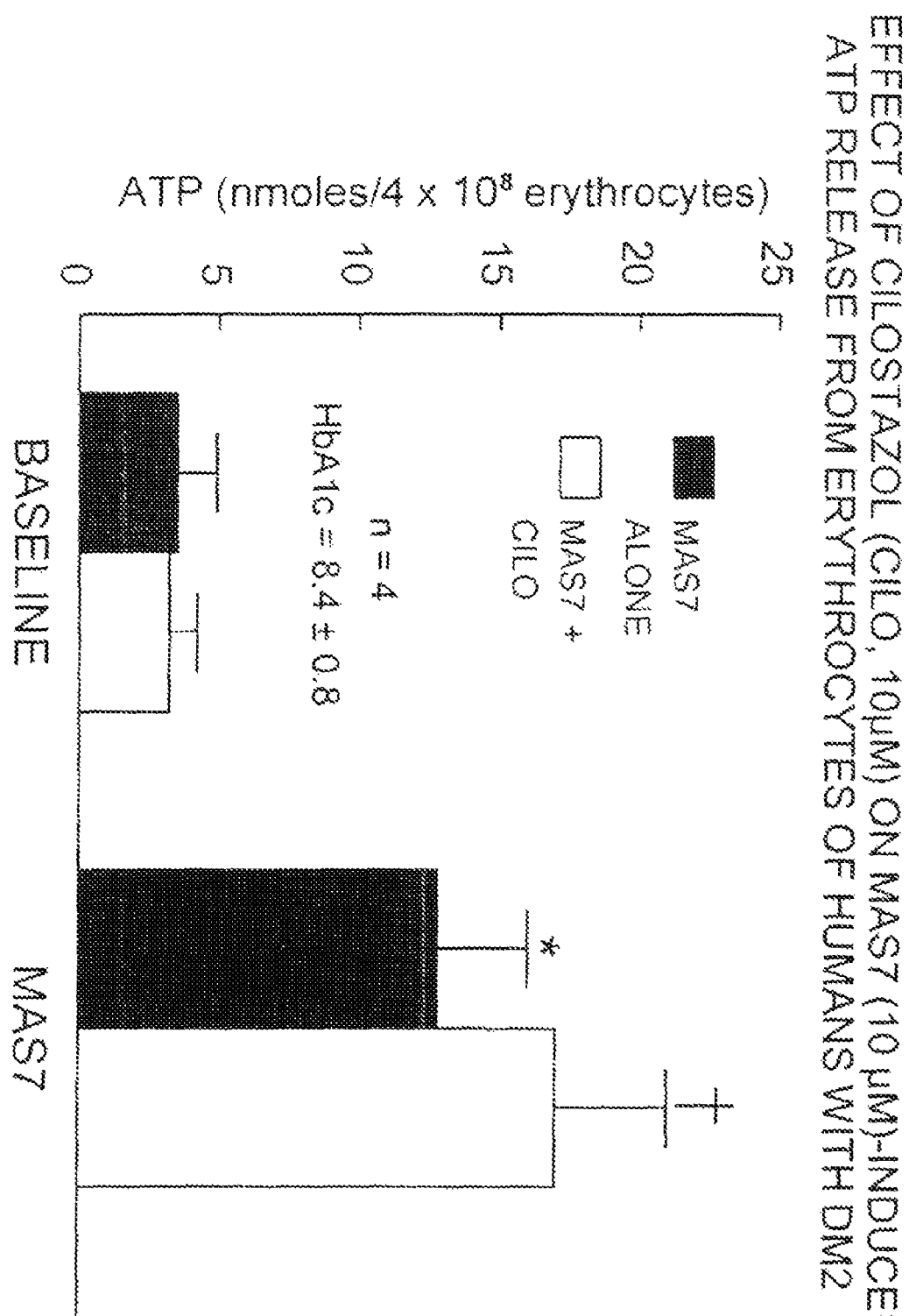
FIG. 20 depicts the effect of cilostazol on Mas7-induced ATP release by RBCs derived from humans having type 2 diabetes.

Protocol B: To demonstrate that selective PDE3 inhibitors and non-hydrolysable cGMP analogs increase erythrocyte cAMP accumulation and ATP release in response to physiological and pharmacological stimuli, washed erythrocytes were incubated with either of the active cGMP analogs, 8-BromocGMP or SpcGMP (50 or 100 µM) or the selective PDE3 inhibitors cilostazol (10, 30, or 100 µM) or milrinone (10 or 30 µM) [39, 54, 69]. After 30 min, the cells were incubated with either iloprost (1 µM), isoproterenol (10 µM), MAS7 (10 µM) or exposed to reduce O2 tension and cAMP accumulation and ATP release was determined. Control experiments: Identical experiments were performed with the vehicles for the various inhibitors. In addition, since PDE4 and PDE5 can be inhibited by high concentrations of milrinone and cilostazol, respectively, separate studies were performed in which erythrocytes were incubated with rolipram (30 µM), a highly selective PDE 4 inhibitor (see FIG. 16) [33, 39] prior to physiological and pharmacological stimulation. The concentrations chosen for rolipram and sildenafil PDE are those reported to be specific for the PDEs indicated.

Protocol C: To demonstrate that PDE3 inhibitors and non-hydrolysable cGMP analogs oppose insulin-induced inhibition of erythrocyte cAMP accumulation and ATP release in response to physiological and pharmacological stimuli, washed erythrocytes were incubated with either 8-Bromo-cGMP, SpcGMP, cilostazol or milrinone [33, 54] along with the insulin at the concentrations determined to be most effective for inhibition of cAMP accumulation and ATP release. After 30 min, the cells were incubated with either iloprost (1 µM), isoproterenol (10 µM), MAS7 (10 µM) or exposed to reduced O2 tension and cAMP accumulation and ATP release were determined.

Results: The presence of PDE3 in the erythrocyte membrane was demonstrated by Western analysis (FIG. 3) and suggests a novel role for this PDE in erythrocyte physiology. PDE3 was shown herein to play an important role in the regulation of cAMP levels leading to alterations in ATP release. It was shown herein that insulin inhibits ATP release via its ability to stimulate PDE3 activity and limit cAMP accumulation. It was also shown herein that inhibition of PDE3 activity increased cAMP accumulation and ATP release in response to physiological and pharmacological stimuli. The inventors conclude that inhibitors of PDE3 prevent insulin-induced reductions in cAMP accumulation and ATP release in response to physiological and pharmacological stimuli. Thus, it is reasonable to expect that the inhibition of PDE3 activity presents a novel approach to the prevention and treatment of the vascular complications associated with prediabetes.

Example 5

General Methods

Generation of Washed Erythrocytes: Human blood was obtained by venipuncture in a syringe containing heparin (500 units) and was centrifuged at 500×g for 10 minutes at 4° C. The plasma, buffy coat, and uppermost erythrocytes were removed by aspiration and discarded. The remaining erythrocytes were washed three times in buffer containing 21.0 mM Tris-HCl, 4.7 KCl, 2.0 mM CaCl2, 140.5 mM NaCl, 1.2 mM MgSO4, 0.1% dextrose, and 0.5% bovine albumin fraction V, final pH 7.4. The hematocrit of the washed erythrocytes was determined.

Preparation of Erythrocyte Membranes: Washed erythrocytes were diluted 1:100 with ice-cold buffer containing 5 mM Tris-HCl, 2 mM EDTA, pH 7.4, and stirred at 4° C. for 15 minutes. The lysate was centrifuged at 30,000×g for 15 minutes at 4° C. The supernatant was removed and discarded. The pellet containing the erythrocyte membranes was washed two times with icecold buffer and centrifuged and the membranes were re-suspended in ice-cold buffer and frozen at −80° C. Membrane protein concentrations were determined using the BCA Protein Assay.

Preparation of Platelets for Western Analysis: Whole blood was centrifuged at 400×g for 10 minutes at 4° C. The supernatant was collected and 0.5 ml heparin and 1 mg/ml EDTA were added and re-centrifuged for 40 minutes at 200×g at 4° C. The platelet-rich-plasma was collected and centrifuged at 1,400×g for 20 minutes at 4° C. The supernatant was discarded and 200 ml of Western lysis buffer (25 mM HEPES, 300 mM NaCl, 10 mM EDTA, 1.5 mM MgCl2.6H2O, 20 mM β-glycerophophate, 0.1 mM sodium vanadate, 1% Triton X-100) was added to pellet followed by sonication (10 s) and, after 15 minutes on ice, centrifugation at 14,000×g for 20 minutes at 4° C. Platelet protein concentrations were determined using the BCA Protein Assay.

Western Analysis: Erythrocyte membranes or platelets were solubilized in SDS buffer (8% SDS, 60% glycerol, 0.25 M Tris HCl (pH 6.8), 0.004% bromophenol blue, and 400 mM dithiothreitol), boiled, and loaded onto a pre-cast 7.5% gel and subjected to electrophoresis at 150 volts for 90 min and transferred to a polyvinylidene difluoride (PVDF) membrane (100 volts for 60 min) in buffer containing 25 mM Tris-base, 192 mM glycine, and 10% methanol. Membranes were blocked overnight with 5% non-fat dry milk in PBS containing 0.1% Tween-20, immunoblotted with a primary antibody directed against protein of interest followed by incubation with an appropriate secondary antibody in 1% non-fat dry milk and visualized using enhanced chemiluminesence.

Measurement of ATP: ATP was measured using the luciferin-luciferase assay. A 200 µL sample of an erythrocyte suspension was injected into a cuvette containing 100 µL of 10 mg/ml crude firefly tail extract and 100 µL of a 0.5 mg/ml solution of D-luciferin. The light emitted from the reaction of ATP with the crude firefly tail extract was measured using a luminometer designed to detect a wavelength of 565 nm. The peak light emitted was compared to an ATP standard curve generated on the day of the experiment.

Measurement of Total Intracellular ATP: A known number of erythrocytes was lysed in distilled water at room temperature. ATP in the lysate, diluted 8,000 fold, was measured using ATP assay and the values normalized to ATP concentration per erythrocyte.

Measurement of Hemoglobin: Erythrocyte suspensions used to measure ATP were centrifuged at 500×g for 10 minutes at 4° C. The amount of hemoglobin present in the supernatant was determined by measurement of absorbance at 405 nm (oxyhemoglobin).

Measurement of cAMP: 1 ml of erythrocyte suspension was added to 4 ml of ice cold ethanol containing 1 mM HCl and the mixture was centrifuged at 21,000×g for 10 minutes at 4° C. The supernatant was removed and stored overnight at −20° C. to precipitate remaining proteins. Samples were centrifuged a second time at 3,700×g for 10 minutes at 4° C. The supernatant was removed and dried under vacuum centrifugation. Concentrations of cAMP were determined by EIA.

Exposure of Erythrocytes to Reduced Oxygen Tension: Washed erythrocytes were diluted in Krebs buffer containing bicarbonate (4.7 KCl, 2.0 mM CaCl2, 140.5 mM NaCl, 1.2 mM MgSO4) and equilibrated for 30 minutes in a tonometer (15% O2, 5% CO2, balance N2) (normoxia). Erythrocytes were then exposed to hypoxia by changing the equilibrating gas to 5% O2, 5% CO2, balance N2. ATP released from the erythrocytes as well as pH and blood gas tensions were determined at 5, 10 and 15 min after exposure to the various gas tensions. In separate studies, samples were collected into acidified ethanol for cAMP measurement.

Determination of Leukocyte and Platelet Contamination of Erythrocyte Preparations: Smears of the concentrated erythrocyte preparations were microscopically examined for leukocytes using a commercial kit (Leukostat). The absence of platelet contamination of membrane preparations was determined by the absence of the platelet protein CD-41 as determined by Western analysis.

Phosphodiesterase Activity Assay: In microcentrifuge tubes, a 7.5 µL aliquot of erythrocyte membrane preparation was incubated with 30 µL of cAMP substrate, 7.5 ml of buffer (10 mM Tris-HCl, pH 7.4), and 15 µL of insulin or various PDE inhibitors at 37° C. At 0, 5, 10, 20, 30, 45, 60 and 90 min, samples were centrifuged at 13,000×g for 10 min and the supernatant collected. Aliquots (50 µL) were mixed with *C. atrox* venom (15 µL) and allowed to incubate for 30 minutes at 30° C. in a microtiter plate after which 100 µL of Biomol Green™ Reagent was added. After agitation (30 min) for color development, the intensity at 620 nm was determined.

Data Analysis: Statistical significance between experiments was determined using an analysis of variance (ANOVA). In the event that the F ratio indicates that a change has occurred, a Fisher's LSD test was done to identify individual differences. Results were reported as means+/−the standard error from the mean (SEM).

What is claimed is:

1. A method of identifying a drug candidate that increases ATP release from a stimulated red blood cell (RBC), the method comprising:
   contacting a first RBC with the drug candidate;
   stimulating the first RBC via a heterotrimeric G protein, wherein the heterotrimeric G protein is selected from the group consisting of Gs and Gi;
   measuring ATP released by the first RBC;
   stimulating a second RBC via a heterotrimeric G protein, wherein the heterotrimeric G protein is selected from the group consisting of Gs and Gi;
   measuring ATP released by the second RBC; and
   comparing the ATP released by the first RBC to the ATP released by the second RBC, wherein the drug candidate is identified if the ATP released by the first RBC is significantly more than the ATP released by the second RBC.

2. The method of claim 1, wherein the drug candidate is a phosphodiesterase inhibitor.

3. The method of claim 2, wherein the phosphodiesterase inhibitor is a phosphodiesterase isoform 3 inhibitor.

4. The method of claim 1, wherein the stimulating step is selected from the group consisting of reduced $O_2$ tension, mechanical deformation, mastoparan 7, iloprost, isoproterenol, and combinations thereof.

5. The method of claim 1, further comprising incubating the first RBC and the second RBC with insulin or an insulin analog before contacting the first RBC with the drug candidate.

6. The method of claim 5, wherein the insulin or the insulin analog is from about 0.1 nM to about 1 μM.

* * * * *